US006436234B1

(12) United States Patent
Chen et al.

(10) Patent No.: US 6,436,234 B1
(45) Date of Patent: Aug. 20, 2002

(54) WET-RESILIENT WEBS AND DISPOSABLE ARTICLES MADE THEREWITH

(75) Inventors: Fung-jou Chen; Mark Alan Burazin, both of Appleton; Michael Alan Hermans, Neenah; David Henry Hollenberg, Kaukauna; Richard Joseph Kamps, Wrightstown; Bernhardt Edward Kressner; Jeffrey Dean Lindsay, both of Appleton, all of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 08/912,906

(22) Filed: Aug. 15, 1997

Related U.S. Application Data

(63) Continuation-in-part of application No. 08/614,420, filed on Mar. 8, 1996, now abandoned, which is a continuation-in-part of application No. 08/310,186, filed on Sep. 21, 1994, now abandoned.

(51) Int. Cl.[7] .............................................. D21H 27/02
(52) U.S. Cl. ........................... 162/109; 162/9; 442/385; 442/389; 442/412; 442/413; 428/153; 428/156
(58) Field of Search ................................. 442/385, 389, 442/412, 413; 604/378, 379; 428/153, 156; 162/9, 109

(56) References Cited

U.S. PATENT DOCUMENTS

| | | | |
|---|---|---|---|
| 3,339,550 A | 9/1967 | Van Haaften | 128/290 |
| 3,556,932 A | 1/1971 | Coscia et al. | 162/166 |
| 3,556,933 A | 1/1971 | Williams et al. | 162/167 |
| 3,700,623 A | 10/1972 | Keim | 260/80.3 R |
| 3,772,076 A | 11/1973 | Keim | 117/155 R |
| 3,885,158 A | 5/1975 | Flutie et al. | 250/440 |
| 3,899,388 A | 8/1975 | Petrovich et al. | 162/164 |
| 4,129,528 A | 12/1978 | Petrovich et al. | 260/823 |
| 4,147,586 A | 4/1979 | Petrovich et al. | 162/135 |
| 4,222,921 A | 9/1980 | Van Eenam | 260/29.6 H |
| 4,388,075 A | 6/1983 | Mesek et al. | 604/385 |
| 4,500,916 A | 2/1985 | Damico | 604/389 |
| 4,675,394 A | 6/1987 | Solarek et al. | 536/43 |
| 4,699,823 A | 10/1987 | Kellenberger et al. | 428/219 |
| 4,938,754 A | 7/1990 | Mesek | 604/385.2 |
| 4,940,464 A | 7/1990 | Van Gompel et al. | 604/396 |
| 4,981,557 A * | 1/1991 | Bjorkquist | 162/168.2 |
| 5,008,344 A | 4/1991 | Bjorkquist | 525/328.2 |
| 5,048,589 A | 9/1991 | Cook et al. | 162/109 |
| 5,069,548 A | 12/1991 | Boehnlein | 356/376 |
| 5,085,736 A | 2/1992 | Bjorkquist | 162/168.2 |
| 5,129,988 A | 7/1992 | Farrington, Jr. | 162/123 |
| 5,147,343 A | 9/1992 | Kellenberger | 604/368 |
| 5,190,563 A | 3/1993 | Herron et al. | 8/120 |
| 5,192,606 A | 3/1993 | Proxmire et al. | 428/284 |
| 5,217,445 A | 6/1993 | Young et al. | 604/381 |
| 5,360,420 A * | 11/1994 | Cook et al. | 604/378 |
| 5,364,382 A | 11/1994 | Latimer et al. | 604/378 |
| 5,386,595 A | 2/1995 | Kuen et al. | 2/400 |
| 5,399,412 A * | 3/1995 | Sudall et al. | 428/153 |
| 5,409,572 A * | 4/1995 | Kershaw et al. | 162/109 |
| 5,411,636 A | 5/1995 | Hermans | 162/109 |
| 5,429,686 A * | 7/1995 | Chiu et al. | 139/383 A |
| 5,486,166 A | 1/1996 | Bishop et al. | 604/366 |
| 5,490,846 A | 2/1996 | Ellis et al. | 604/366 |
| 5,492,598 A | 2/1996 | Hermans et al. | 162/113 |
| 5,509,915 A | 4/1996 | Hanson et al. | 604/378 |
| 5,549,592 A * | 8/1996 | Fries et al. | 604/389 |
| 5,624,532 A * | 4/1997 | Trokhan et al. | 162/111 |

FOREIGN PATENT DOCUMENTS

| | | | |
|---|---|---|---|
| JP | 3-185197 A | 8/1991 | D21H/17/28 |
| JP | 10-272710 | * 10/1998 | |

OTHER PUBLICATIONS

AATCC Test Method 66–1990, "Wrinkle Recovery of Fabrics: Recovery Angle Method," *Technical Manual of the American Association of Textile Chemists and Colorists*, 1995, pp. 99–100.

Adams, Kurt L., Bernard Miller, and Ludwig Rebenfeld, "Forced In–Plane Flow of an Epoxy Resin in Fibrous Networks," *Polymer Engineering And Science*, Mid–Nov., 1986, vol. 26, No. 26, pp. 1434–1441.

Back, Ernst L., "The Pore Anisotropy of Paper Products and Fibre Building Boards," *Svensk Papperstidning* arg. 69, Nr. 7, Apr. 15, 1996, pp. 219–224.

Bear, Jacob, "Dynamics of Fluids in Porous Media," American Elsevier Publishing Company, Inc., New York, NY, 1972, pp. 136–151.

Bieman, Leonard H., Kevin G. Harding, and Albert Boehnlein, "Absolute Measurement Using Field Shifted Moiré", *Optics, Illumination and Image Sensing for Machine Vision VI*, SPIE Proceedings Series, Nov. 14–15, 1991, vol. 1614, pp. 259–264.

Bowden, Edward V., "Non–Contact Drying and Turning—the 'On Machine' Technology of the Nineties," *Appita*, vol. 44, No. 1, Jan. 1991, pp. 41–46.

Cadeyes Product Guide, Medar, Inc., Farmington Hills, MI, 1994, pp. 1–19.

(List continued on next page.)

Primary Examiner—Terrel Morris
Assistant Examiner—John J. Guarriello
(74) Attorney, Agent, or Firm—Gregory E. Croft

(57) ABSTRACT

Paper sheets useful for tissues, paper towels, napkins, disposable absorbent products and the like can be made to exhibit a high degree of wet resiliency. This property is achieved by using a combination of high yield pulp fibers (such as bleached chemithermomechanical pulp fibers) and a wet strength agent in an uncreped throughdrying process. The resulting product, when wetted, can spring back after being crumpled in one's hand.

69 Claims, 20 Drawing Sheets

OTHER PUBLICATIONS

Dullien, F, A. L. "Porous Media: Fluid Transport and Pore Structure," Academic Press, New York, 1979, pp. 78–83.

Lindsay, Jeffrey D. and Jill R. Wallin, "Characterization of In–Plane Fluid Flow in Paper," *AIChE Proceedings 1989 and 1990 Forest Products Symposium,* Tappi Press, Atlanta, GA, 1992, pp. 121–129.

Horstmann, Diane H., Jeffrey D. Lindsay, and Robert A. Stratton, "Using Edge–Flow Tests to Examine the In–Plane Anisotropic Permeability of Paper," *Tappi Journal,* 74(4), Apr. 1991, pp. 241–247.

Lindsay, Jeffrey D., "The Anisotropic Permeability of Paper," *Tappi Journal,* 73(5), May 1990, pp. 223–229.

Lindsay, Jeffrey D., "The Anisotropic Permeability of Paper: Theory, Measurements, and Analytical Tools," *IPC Technical Paper Series No. 298,* Jul. 1998, pp. 1–50.

Lindsay, Jeffrey D., "Relative Flow Porosity in Fibrous Media: Measurements and Analysis, Including Dispersion Effects," *Tappi Journal,* vol. 77, No. 6, Jun. 1994, pp. 225–239.

Lindsay, Jeffrey D. and Paul H. Brady, "Studies of Anisotropic Permeability With Applications to Water Removal in Fibrous Webs: Part 1," *Tappi Journal,* vol. 76, No. 9, Sep. 1993, pp. 119–125.

Lindsay, Jeffrey D. and Paul H. Brady, "Studies of Anisotropic Permeability With Applications to Water Removal in Fibrous Webs: Part 2," *Tappi Journal,* vol. 76, No. 11, Nov. 1993, pp. 167–174.

Mummery, Leigh, "Surface Texture Analysis: The Handbook," published by Hommelwerke GmbH, Muhlhausen, Germany, 1990, pp. 28–29.

* cited by examiner

Del z: 0.304 mm

Del z: 0.134 mm

P10: 0.233 mm

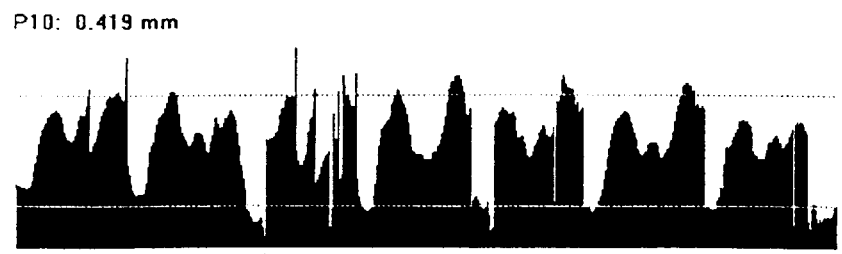
FIG. 4A
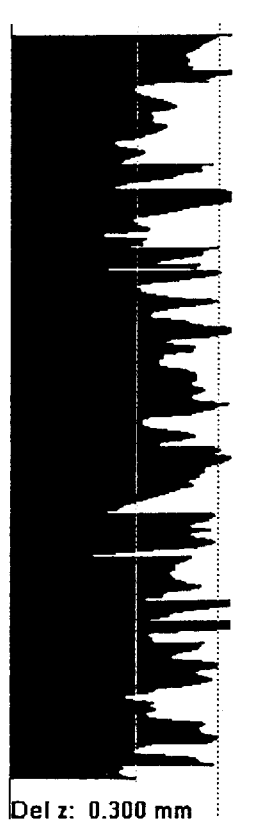 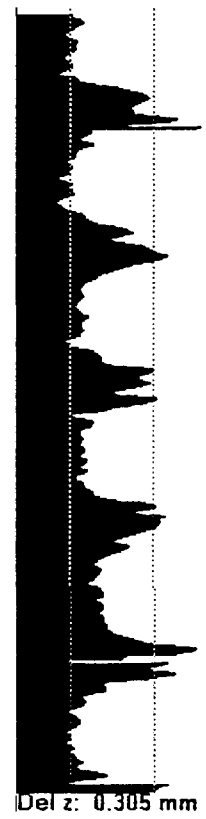
FIG. 4B   FIG. 4C
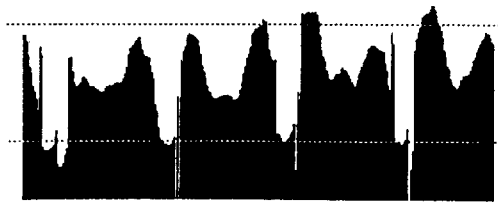
FIG. 5

| Present invention sample numbers | Fiber | BW (single ply) | Kymene, lb/ton of fiber | Fabric type | Rush transfer, % |
|---|---|---|---|---|---|
| U1 | Spruce BCTMP | 30 | 20 | T116-3 | 15 |
| U2 | Spruce BCTMP | 60 | 20 | T116-3 | 30 |
| U3 | Spruce BCTMP | 40 | 10 | T 116-3 | 35 |
| U4 | Spruce BCTMP | 40 | 20 | T 116-3 | 35 |
| U5 | Spruce BCTMP | 60 | 10 | T 116-3 | 35 |
| U6 | Spruce BCTMP | 60 | 20 | T 116-3 | 35 |
| U7 | Spruce BCTMP | 60 | 10 | T 116-3 | 15 |
| U8 | 25% Spruce BCTMP, 75% north. SW kraft | 60 | 10 | T 116-3 | 15 |
| U9 | Spruce BCTMP | 60 | 10 | T 116-1 | 15 |
| U10 | Spruce BCTMP | 40 | 30 | T 116-3 | ? |

FIG. 10

| Related Art Materials | BW, gsm | Sheets | MR | Initial bulk, cc/g | Comp. bulk, cc/g | Final bulk, cc/g | Spring-back | LER |
|---|---|---|---|---|---|---|---|---|
| Viva Ultra | 62 | 2 | 1.00 | 13.0 | 4.3 | 6.7 | 0.515 | 0.475 |
| Brawny, 1994 | 47 | 3 | 1.26 | 12.2 | 3.7 | 7.5 | 0.614 | 0.635 |
| Bounty Quilted | 38 | 2 | 1.25 | 21.4 | 5.8 | 14.1 | 0.657 | 0.623 |
| Bounty Quilted | 39 | 3 | 1.18 | 20.7 | 5.6 | 13.8 | 0.667 | 0.626 |
| Printed Bounty | 60 | 2 | 1.09 | 21.6 | 5.5 | 13.0 | 0.604 | 0.604 |
| Air-laid Softwood | 129 | 1 | 0.93 | 27.5 | 6.3 | 11.5 | 0.417 | 0.494 |
| Other Uncreped Materials | | | | | | | | |
| Surpass | 41 | 3 | 1.27 | 11.6 | 5.2 | 9.2 | 0.793 | 0.720 |
| Surpass | 40 | 3 | 1.08 | 12.0 | 5.3 | 9.6 | 0.797 | 0.673 |
| Surpass | 41 | 3 | 1.13 | 11.5 | 5.2 | 9.1 | 0.793 | 0.720 |
| O2 | 38 | 3 | 1.22 | 13.5 | 5.8 | 10.3 | 0.762 | 0.623 |
| O3 | 60 | 2 | 1.12 | 12.9 | 6.8 | 10.6 | 0.825 | 0.658 |
| O4 | 59 | 2 | 1.09 | 10.2 | 5.2 | 8.1 | 0.796 | 0.664 |
| Present Invention | | | | | | | | |
| U2 | 57 | 2 | 1.21 | 15.2 | 8.7 | 14.1 | 0.929 | 0.835 |
| U3 | 39 | 3 | 1.58 | 23.1 | 9.6 | 18.3 | 0.793 | 0.713 |
| U3 | 40 | 3 | 1.18 | 22.6 | 9.7 | 18.0 | 0.798 | 0.716 |
| U4 | 40 | 3 | 1.33 | 21.8 | 9.7 | 18.0 | 0.829 | 0.740 |
| U5 | 55 | 2 | 1.16 | 16.7 | 9.4 | 14.7 | 0.880 | 0.807 |
| U5 | 58 | 2 | 1.18 | 15.3 | 9.2 | 13.8 | 0.903 | 0.793 |
| U6 | 58 | 2 | 1.24 | 16.2 | 9.7 | 14.3 | 0.883 | 0.814 |
| U6 | 58 | 2 | 1.34 | 16.3 | 9.6 | 14.5 | 0.895 | 0.833 |
| U7 | 59 | 2 | 1.08 | 14.9 | 8.3 | 12.8 | 0.861 | 0.797 |
| U7 | 58 | 2 | 1.19 | 16.0 | 8.0 | 13.5 | 0.842 | 0.768 |
| U8 | 58 | 2 | 1.16 | 13.2 | 7.5 | 11.1 | 0.839 | 0.718 |
| U9 | 59 | 2 | 1.12 | 13.1 | 7.3 | 11.7 | 0.889 | 0.761 |
| U10 | 37 | 3 | 1.16 | 24.2 | 11.6 | 20.2 | 0.835 | 0.755 |
| U10 | 38 | 3 | 1.22 | 23.6 | 10.9 | 19.1 | 0.809 | 0.735 |

FIG. 11

| Sample | Dry BW, gsm | Wet weight, g | Oven dry weight, g | Moisture ratio | Initial thickness @ 0.025 psi | Thickness at 2 psi, in | Final thickness, in | Initial bulk, cc/g | Wet Comp. Bulk, cc/g | Final bulk, cc/g | Spring-back | LER |
|---|---|---|---|---|---|---|---|---|---|---|---|---|
| CQ-A | 155 | 1.34 | 0.644 | 1.08 | 0.226 | 0.051 | 0.115 | 35.9 | 8.11 | 18.3 | 0.509 | 0.64 |
| CQ-A2 | 153 | 1.39 | 0.637 | 1.18 | 0.176 | 0.046 | 0.109 | 28.3 | 7.40 | 17.5 | 0.619 | 0.723 |
| CQ-A3 | 150 | 1.24 | 0.625 | 0.98 | 0.159 | 0.043 | 0.099 | 26.1 | 7.05 | 16.2 | 0.623 | 0.736 |
| CQ-B | 107 | 1.02 | 0.445 | 1.29 | 0.15 | 0.036 | 0.081 | 34.5 | 8.29 | 18.6 | 0.54 | 0.641 |
| CQ-C | 184 | 1.565 | 0.766 | 1.04 | 0.277 | 0.059 | 0.140 | 37.0 | 7.89 | 18.7 | 0.505 | 0.634 |
| CQ-D | 214 | 1.98 | 0.891 | 1.22 | 0.342 | 0.067 | 0.174 | 39.3 | 7.70 | 20.0 | 0.509 | 0.599 |
| CQ-E | 201 | 1.82 | 0.835 | 1.18 | 0.285 | 0.064 | 0.146 | 35.0 | 7.85 | 17.9 | 0.512 | 0.636 |
| CQ-F | 87 | 0.741 | 0.361 | 1.05 | 0.101 | 0.027 | 0.065 | 28.7 | 7.66 | 18.5 | 0.644 | 0.713 |
| HBAFF-1 | 121 | 1.057 | 0.502 | 1.11 | 0.168 | 0.033 | 0.073 | 34.3 | 6.73 | 14.9 | 0.435 | 0.566 |
| HBAFF-2 | 94 | 0.866 | 0.392 | 1.21 | 0.141 | 0.025 | 0.062 | 36.8 | 6.53 | 16.2 | 0.44 | 0.599 |
| HPZ | 95 | 0.853 | 0.397 | 1.15 | 0.113 | 0.022 | 0.052 | 29.2 | 5.68 | 13.4 | 0.46 | 0.565 |

FIG. 13

| Present invention sample numbers | Fiber | BW (single ply) | Sheets or layers used | Kymene, lb/ton of fiber | Fabric type | Rush transfer, % | In-plane permeab., m² x 10¹⁰ | Wet bulk at 0.8 psi, cc/g |
|---|---|---|---|---|---|---|---|---|
| U3 | Spruce BCTMP | 40 | 2 | 10 | T 116-3 | 35 | 1.05 | 10.31 |
| U4 | Spruce BCTMP | 40 | 2 | 20 | T 116-3 | 35 | 1.19 | 10.99 |
| U4b | Spruce BCTMP | 40 | 2 | 20 | T 116-3 | 35 | 1.56 | 11.79 |
| U4c | Spruce BCTMP | 40 | 3 | 20 | T 116-3 | 35 | 1.22 | 11.46 |
| U4d | Spruce BCTMP | 40 | 4 | 20 | T 116-3 | 35 | 1.05 | 11.20 |
| U5 | Spruce BCTMP | 60 | 2 | 10 | T 116-3 | 35 | 1.26 | 9.89 |
| U6 | Spruce BCTMP | 60 | 2 | 20 | T 116-3 | 35 | 1.87 | 10.53 |
| U7 | Spruce BCTMP | 60 | 2 | 10 | T 116-3 | 15 | 0.55 | 8.46 |
| U8 | 25% Spruce BCTMP, 75% north. SW kraft | 60 | 2 | 10 | T 116-3 | 15 | 0.84 | 7.99 |
| U9 | Spruce BCTMP | 60 | 2 | 10 | T 116-1 | 15 | 0.60 | 7.74 |
| Other samples | | | | | | | | |
| P1 | Surpass towel | 40 | 2 | | | | 0.41 | 5.43 |
| P2 | Quilted Bounty | 40 | 2 | | | | 0.34 | 5.70 |
| P3 | HBAFF air-laid pad | 229 | 1 | | | | 0.30 | 7.71 |
| P4 | Curly-Q fiber, air-laid | 245 | 1 | | | | 0.43 | 8.87 |
| P5 | Birch BCTMP UCTAD | 60 | 1 | 0 | | | 0.05 | 5.79 |
| P6 | Untreated softwood fluff | 179 | 2 | | | | 0.03 | 6.59 |
| P7 | Air-laid CR-1654 | 206 | 1 | | | | 0.043 | 6.74 |

FIG. 14

| Code | Insult 1 time, sec | Insult 2 time, sec | Insult 3 time, sec | Sum of insult times | Dry weight |
|---|---|---|---|---|---|
| Surpass | 35. | 215.9 | 358.1 | 609. | 9.3 |
| Bounty | 10.3 | 26.8 | 117.4 | 155. | 8.83 |
| U3 | 4.3 | 6.9 | 13.5 | 25. | 10.77 |
| U4 | 7.0 | 6.7 | 11.2 | 25. | 10.46 |
| U5 | 9.5 | 16.9 | 24.5 | 51. | 10.45 |
| U6 | 11.4 | 15.3 | 21.8 | 49. | 10.62 |
| U7 | 11.4 | 24.7 | 50.4 | 86. | 10.72 |
| U8 | 12.7 | 26.1 | 53.7 | 92. | 10.24 |

FIG. 15

Test Material

Dry Wipe Residual Data

| Sample Identification | Total Area (mm²) | % Coverage | Mass Factor (area*darkness/1000) |
|---|---|---|---|
| 1. Surpass | 3222 | 29.0 | 58.0 |
| 2. BOUNTY® | 3684 | 53.4 | 57.0 |
| 3. CHF, 40 gsm, 10 lb/t | 1421 | 16.6 | 17.5 |
| 4. " , " " , 20 " | 971 | 12.9 | 11.0 |
| 5. " , 60 " , 10 " | 1002 | 15.1 | 9.7 |
| 6. " , " " , 20 " | 780 | 12.2 | 8.3 |
| 7. EFU, " " , 10 " | 892 | 11.0 | 7.5 |
| 8. CHF, " " , 25/75, Spr./LL19, 10 lb/t | 708 | 10.3 | 11.0 |

FIG. 20

Wet Wipe Residual Data

| Sample Identification | Total Area (mm²) | % Coverage | Mass Factor (area*darkness/1000) |
|---|---|---|---|
| 1. Surpass | 1086 | 22.0 | 8.87 |
| 2. BOUNTY® | 1815 | 35.4 | 16.4 |
| 3. CHF, 40 gsm, 10 lb/t | 581 | 12.2 | 4.06 |
| 4. " , " " , 20 " | 652 | 13.6 | 5.00 |
| 5. " , 60 " , 10 " | 419 | 8.72 | 2.76 |
| 6. " , " " , 20 " | 476 | 10.3 | 3.46 |
| 7. EFU, " " , 10 " | 657 | 13.6 | 3.28 |
| 8. CHF, " " , 25/75, Spr./LL19, 10 lb/t | 576 | 11.8 | 4.16 |

FIG. 21

| Sample Identification | Mean Volume-Weighted Pore Length | Thickness Variation (% COV) |
|---|---|---|
| 1. Surpass | 136 | 14.9 |
| 2. BOUNTY® | 484 | 43.9 |
| 3. CHF, 40 gsm, 10 lb/t | 642 | 8.7 |
| 4. " , " ,20 " | 930 | 17.8 |
| 5. " ,60 " ,10 " | 788 | 15.0 |
| 6. " , " ,20 " | 849 | -- |
| 7. EFU, " ,10 " | 772 | -- |
| 8. CHF, " , 25/75, Spr./LL19,10 lb/t | 697 | 16.8 |

Reject } Accept } Reject }

A typical photo

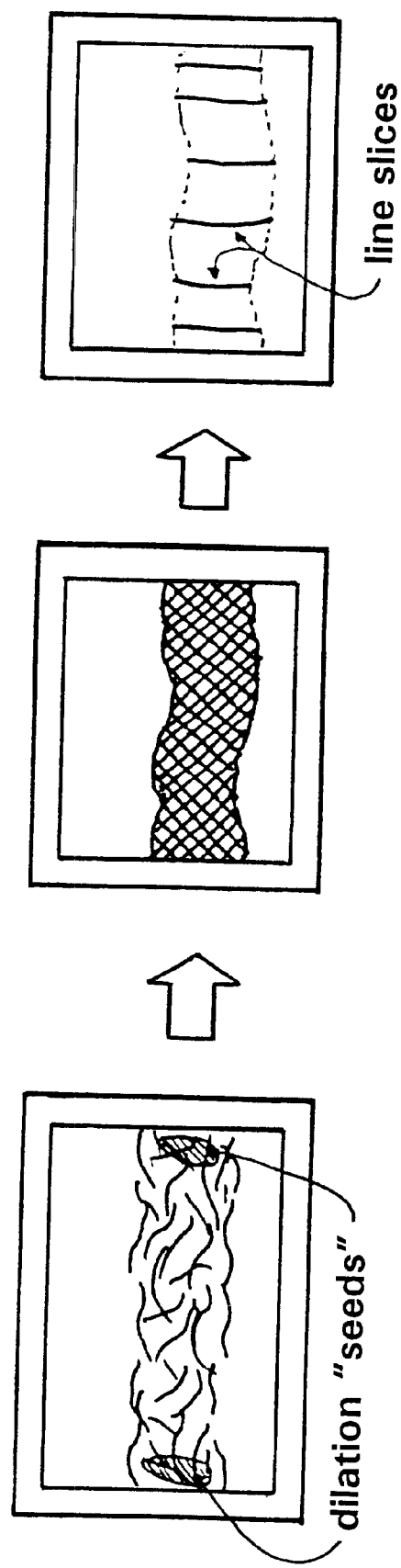

WET-RESILIENT WEBS AND DISPOSABLE ARTICLES MADE THEREWITH

This application is a continuation-in-part of application Ser. No. 08/614,420, entitled "WET-RESILIENT WEBS AND DISPOSABLE ARTICLES MADE THEREWITH" AND FILED IN THE U.S. Patent and Trademark Office on Mar. 8, 1996, now abandoned which application is a continuation-in-part of application Ser. No. 08/310,186 entitled "WET-RESILIENT WEBS" and filed in the U.S. Patent and Trademark Office on Sep. 21, 1994, now abandoned. The entirely of this application is hereby incorporated by reference.

BACKGROUND OF THE INVENTION

In the manufacture of absorbent paper products such as facial tissue, bath tissue, paper towels, napkins and the like, many different sheet properties influence the performance of the particular product being made. Softness, strength, absorbency, bulk and the like are often the subject of improvements. However, a property of tissue-related products is that when wetted and crumpled in the hand, they essentially collapse into a dense wet mass. Stated another way, such tissue products have a low wet compressive modulus, low bending modulus and low wet resiliency. These properties are undesirable for such products when used to wipe up liquids because, once saturated, they lose their designed structure and thus much of their functionality.

Similar problems can be found with some disposable absorbent articles. Generally, disposable absorbent articles include, in their construction, an absorbent core positioned between a liquid-permeable cover or topsheet layer and a liquid-impermeable baffle or backsheet layer. The cover material is generally designed to allow body exudates to permeate through the cover so that the absorbent core can absorb the fluids. The baffle or backsheet material is generally fluid impermeable and is positioned so that it is away from the body. The absorbent core serves to store fluid that contacts the article. An additional layer of material, termed a transfer layer or surge layer, may also be present between the absorbent core and the liquid-permeable cover. This layer serves to manage the transfer or distribution of the liquid to the absorbent core. Examples of such absorbent articles include products such as diapers, sanitary napkins, training pants, incontinent garments, overnight pads, panty liners, underarm shields, as well as other absorbent devices used for medical purposes such as surgical absorbents. Such articles are designed to absorb body fluids, such as urine, menses, blood, perspiration and other excrement discharged by the body.

One continuing problem with some disposable absorbent articles is that the bodily excretions are usually directed at one portion of the absorbent, whereas the absorptive capacity of the product is spread over a greater area. Localized insults of body fluid may cause a failure of the product because the fluid handling characteristics of the liquid-permeable cover, transfer layer and the absorbent core are inadequate to quickly distribute the fluid throughout the absorbent core material. Such failures are often in part due to the collapse of the low density structure of the various components when wetted. This is a particular problem for cellulosic materials.

Accordingly, there is a need for a wet-resilient web material that can more effectively transfer and/or absorb fluids for use in tissues, towels and absorbent products.

SUMMARY OF THE INVENTION

It has been discovered that papermaking fibers containing high-yield fibers, such as chemithermomechanical pulp fibers, when combined with wet strength additives, can be made into a low-density, three-dimensional sheet or web followed by or incorporating largely noncompressive drying means such that the resulting low density cellulosic sheet has remarkable wet resiliency properties, showing great resistance to wet collapse.

"Noncompressive drying refers to drying methods such as through-air drying; air jet impingement drying; non-contacting drying such as air flotation drying, as taught by E. V. Bowden, Appita Journal, 44(1): 41 (1991); through-flow or impingement of superheated steam; microwave drying and other radiofrequency or dielectric drying methods; water extraction by supercritical fluids; water extraction by nonaqueous, low surface tension fluids; infrared drying; drying by contact with a film of molten metal; and other methods for drying cellulosic webs that do not involve compressive nips or other steps causing significant densification or compression of a portion of the web during the drying process. (Standard dry creping technology is viewed as a compressive drying method since the web must be mechanically pressed onto part of the drying surface, causing significant densification of the regions pressed onto the heated Yankee cylinder.) The three-dimensional sheets of the present invention could be dried with any of the above mentioned noncompressive drying means without causing significant web densification or a significant loss of their three-dimensional structure and their wet resiliency properties.

Preferably, the low-density three-dimensional structure is created in substantial part before the sheet reaches a solids level (dryness level) of about 80% or higher. Creating the low-density three-dimensional structure can be achieved in part through a variety of means, including but not limited to the use of specially treated high-bulk fibers such as curled or chemically treated fibers as an additive in the furnish, including the fibers taught by C. C. Van Haaften in "Sanitary Napkin with Cross-linked Cellulosic Layer," U.S. Pat. No. 3,339,550, issued Sep. 5, 1967, which is hereby incorporated by reference; mechanical debonding means such as differential velocity ("rush") transfer between fabrics or wires, hereafter described; mechanical straining or "wet straining" of the moist web, including the methods taught by M. A. Hermans et al. in U.S. Pat. No. 5,492,598, "Method for Increasing the Internal Bulk of Throughdried Tissue," issued Feb. 20, 1996, herein incorporated by reference, and M. A. Hermans et al. in U.S. Pat. No. 5,411,636, "Method for Increasing the Internal Bulk of Wet-Pressed Tissue," issued May 2, 1995, herein incorporated by reference; molding of the fiber onto a three-dimensional wire or fabric, such as the fabrics disclosed by Chiu et al. in U.S. Pat. No. 5,429,686, "Apparatus for Making Soft Tissue Products," issued Jul. 4, 1995, which is hereby incorporated by reference, including differential velocity transfer onto or from said three-dimensional wire or fabric; wet embossing of the sheet; wet creping; and the optional use of chemical debonding agents.

Products of the present invention have surprisingly high wet resiliency. For example, when the products of this invention are saturated with water and crumpled in one's hand into a ball about the size of a golf ball, and thereafter released, they quickly open up to mostly uncrumple themselves. By contrast, current commercially-available products such as bath tissues and paper towels remain substantially wadded up in a wet ball. It has been further discovered that such sheets, when properly made, can have unexpectedly good fluid handling properties, such as high intake rate, high in-plane permeability, high absorption capacity, and rapid in-plane distribution of liquid, making these materials ideally suited for use in tissues, paper towels and numerous absorbent articles. As used herein, unless otherwise stated, absorbent articles include sanitary napkins and other feminine care products; disposable diapers and related personal care products; training pants; incontinence products; breast pads; poultry pads and meat pads for absorbing blood and meat juices; bed pads for home and hospital use; sweat bands and other perspiration absorbing articles; odor and sweat absorbing pads for use in shoes or garments; and the like. The materials of the present invention can be utilized in numerous articles where fluid is absorbed or entrapped, functioning as fluid surge webs, transfer layers, distribution webs, absorbent cores, absorbent composites, and so forth. The high wet strength and significant large-scale texture of the materials also can serve effectively in preventing the breakup or loss of integrity of weaker, adjacent materials such as fluff pulp or tissue in absorbent articles, allowing the materials of the present invention to serve effectively as means for maintaining or improving the integrity of the absorbent core (superabsorbent/fluff mixture) of absorbent articles such as diapers and the like. Further, the combination of high wet strength, high absorption capacity, and significant surface texture makes these materials ideally suited for cleaning operations such as scrubbing, mopping, and wiping, with possible incorporation into cleaning articles such as mops, wipers, scrub pads, and the like. As used herein, the terms "web" and "sheet" are used interchangeably and mean the same.

The unique properties and characteristics of the sheets of this invention can be quantified by one or more of the following terms, which will hereinafter be described and defined: Overall Surface Depth; wet:dry ratio; Wet Wrinkle Recovery Test; Wet Compressed Bulk; Wet Springback ratio; Loading Energy Ratio; Compression Ratio; In-Plane Permeability; the FIFE Test; Dry Wipe Residual Total Area and Mass Factor; Wet Wipe Residual Total Area and Mass Factor; Mean Volume-Weighted Pore Length; and the Thickness Variation Index. All of these terms relate to the superior performance of the sheets of this invention when used in various product applications.

Hence, in one aspect, the invention resides in a non-compressively dried cellulosic web, such as a through-air-dried web, more specifically an uncreped through-air-dried web, having a density of about 0.3 gram per cubic centimeter or less and a three-dimensional surface having an Overall Surface Depth of about 0.10 millimeter or greater, said web comprising a wet strength agent and at least about 10 dry weight percent high yield pulp fibers, preferably virgin high yield pulp fibers, and more preferably virgin softwood fibers, said three-dimensional surface preferably being created in substantial part by mechanical means prior to reaching a dryness level of about 80 percent, more preferably with the use of through-drying fabrics, and preferably with a rush transfer level exceeding 10 percent.

The basis weight of the webs of this invention can be about 10 grams per square meter (gsm) or greater, more specifically from about 10 to about 80 gsm, still more specifically from about 20 to about 60 gsm, and still more specifically from about 30 to about 50 gsm.

The fiber composition of the webs of this invention can have from about 10 to about 100 percent wood pulp fibers, particularly containing about 70 percent or greater, more specifically about 80 percent or greater, more specifically about 90 percent or greater, and still more specifically about 95 percent wood pulp fibers or greater. Additionally, it is preferred that the fiber composition of the webs of this invention comprise about 70 percent or greater softwood fibers, more specifically about 80 percent or greater, and still more specifically about 90 percent or greater softwood fibers.

In another aspect, the present invention resides in an absorbent article comprising a backsheet layer, a liquid permeable topsheet layer connected in a superposed relation with the backsheet layer, and at least one cellulosic web as described above sandwiched between the topsheet layer and the backsheet layer. The cellulosic web can also serve as an absorbent core material to retain and store liquid, particularly when incorporated into the absorbent article in multiple plies (such as from about 2 to about 20 or more, more specifically from about 2 to about 5 or 10) or it can serve to receive and distribute liquid to the absorbent core by being positioned in liquid communication with the absorbent. As such the webs of this invention can be used as "transfer" layers, "surge" layers, "distribution" layers and the like.

Representative patents illustrating absorbent products in which the web or sheets of this invention can be used include: U.S. Pat. No. 5,386,595 issued Feb. 7, 1995 to Kuen et al. entitled "Garment Attachment System"; U.S. Pat. No. 4,500,316 issued Feb. 19, 1985 to Damico entitled "Disposable Garment"; U.S. Pat. No. 5,364,382 issued Nov. 15, 1994 to Latimer et al. entitled "Absorbent Structure Having Improved Fluid Surge Management and Product Incorporating Same"; U.S. Pat. No. 4,940,464 issued Jul. 10, 1990 to Van Gompel et al. entitled "Disposable Incontinence Garment or Training Pant"; and copending application Ser. No. 415,382 filed Apr. 3, 1995 in the names of D. Fries et al. entitled "Absorbent Article With Laminated Tape", all of which are herein incorporated by reference.

Although the reasons for the unexpectedly good material properties and product performance results obtained with the present invention are not fully understood, it appears that three factors interact synergistically to yield unusually high wet resiliency performance: (1) a high bulk (low density) three-dimensional structure obtained without significant compression during drying and preferably obtained without creping, (2) high yield pulp fibers, preferably comprising at least about 20 percent of the fiber furnish used to make the sheet; and (3) the use of one or more wet strength resins or agents such that the wet to dry geometric mean tensile strength ratio is about 0.1 or greater. It has been found that if any of these three factors is missing, a wetted sheet will lack the high wet resiliency and/or other properties which are important for many of the uses for the webs of the present invention.

Definition of Terms and Test Procedures

In describing the webs of this invention and their fluid-handling characteristics, a number of terms and tests are used which are described below.

As used herein, "high yield pulp fibers" are those natural papermaking fibers produced by pulping processes providing a yield of about 65 percent or greater, more specifically about 75 percent or greater, and still more specifically from about 75 to about 95 percent. Yield is the resulting amount of processed fiber expressed as a percentage of the initial raw material mass. Such pulping processes include bleached chemithermomechanical pulp (BCTMP), chemithermomechanical pulp (CTMP) pressure/pressure thermomechanical pulp (PTMP), thermomechanical pulp (TMP), thermomechanical chemical pulp (TMCP), high yield sulfite pulps, and high yield kraft pulps, all of which leave the resulting fibers with high levels of lignin. High yield fibers are well known for their stiffness (in both dry and wet states) relative to typical chemically pulped fibers. The cell wall of kraft and other non-high yield fibers tends to be more flexible because lignin, the "mortar" or "glue" on and in part of the cell wall, has been largely removed. The preferred high yield pulp fibers can also be characterized by being comprised of comparatively whole, relatively undamaged fibers, high freeness (250 Canadian Standard Freeness (CFS) or greater, more specifically 350 CFS or greater, and still more specifically 400 CFS or greater), and low fines content (less than 25 percent, more specifically less than 20 percent, still more specifically less that 15 percent, and still more specifically less than 10 percent by the Britt jar test). Webs made with recycled fibers are less likely to achieve the wet resiliency properties of the present invention because of damage to the fibers during mechanical processing. In addition to common papermaking fibers listed above, high yield pulp fibers also include other natural fibers such as milkweed seed floss fibers, abaca, hemp, cotton and the like. Fibers from wood are preferred.

The amount of high yield pulp fibers in the sheet can be at least about 10 dry weight percent or greater, more specifically about 15 dry weight percent or greater, more specifically about 30 dry weight percent or greater, still more specifically about 50 dry weight percent or greater, and still more specifically from about 20 to 100 percent. For layered sheets, these same amounts can be applied to one or more of the individual layers such that the overall unitary web has at least about 10 or 15 percent high yield fibers. Because high yield pulp fibers are generally less soft than other papermaking fibers, in some applications it is advantageous to incorporate them into the middle of the final product, such as placing them in the center layer of a three-layered sheet or, in the case of a two-ply product, placing them in the inwardly-facing layers of each of the two plies.

"Water retention value" (WRV) is a measure that can be used to characterize some fibers useful for purposes of this invention. WRV is measured by dispersing 0.5 grams of fibers in deionized water, soaking overnight, then centrifuging the fibers in a 1.9 inch diameter tube with a 100 mesh screen at the bottom at 1000 G for 20 minutes. The samples are weighed, then dried at 1050 C. for two hours and then weighed again. WRV is (wet weight-dry weight)/dry weight. Fibers useful for purposes of this invention can have a WRV of about 0.7 or greater, more specifically about 0.9 or greater, still more specifically from about 0.9 to about 2. High yield pulp fibers often have a WRV of about 1 or greater.

"Density" can be determined by measuring the caliper of a single sheet using a TMI tester with a load of 0.289 psi. Density is calculated by dividing the caliper by the basis weight of the sheet. The webs of this invention commonly have low, substantially uniform densities (high bulks). Substantial density uniformity can be achieved, for example, by noncompressive drying means such as throughdrying to final dryness without differentially compressing the web. While the webs of this invention have a three-dimensional contour imparted by the topography of a throughdrying fabric, the side-to-side thickness of the web is relatively uniform. In general, the density of the products of this invention can be about 0.3 gram per cubic centimeter or less, more specifically about 0.15 gram or less, still more specifically about 0.1 gram per cubic centimeter or less. It is believed to be important that the absorbent structure, once formed, be dried without substantially reducing the number of wet- resilient interfiber bonds. Throughdrying, which is a common method for drying tissues and towels, is a preferred method of preserving the structure. Absorbent structures made by wet laying followed by throughdrying typically have a density of about 0.1 gram per cubic centimeter, whereas airlaid structures normally used for diaper fluff typically have densities of about 0.05 gram per cubic centimeter. All of such structures are within the scope of this invention.

"Wet strength agents". An integral part of the invention is the material used to immobilize the bonds between the fibers in the wet state. Typically the means by which fibers are held together in paper and tissue products involve hydrogen and sometimes combinations of hydrogen bonds and covalent and/or ionic bonds. In the present invention, it is important to provide a material that will allow bonding of fibers in such a way as to immobilize the fiber to fiber bond points and make them resistant to disruption in the wet state. In this instance the wet state usually will mean when the product is exposed to water or other aqueous solutions, but could also mean exposure to body fluids such as urine, blood, mucus, menses, lymph and other body exudates.

There are a number of materials commonly used in the paper industry to impart wet strength to paper and board that are applicable to this invention. These materials are known in the art as "wet strength agents" and are commercially available from a wide variety of sources. Any material that when added to a paper web or sheet results in providing the sheet with a wet geometric tensile strength:dry geometric tensile strength ratio in excess of 0.1 will, for purposes of this invention, be termed a wet strength agent. Typically these materials are termed either as permanent wet strength agents or as "temporary" wet strength agents. For the purposes of differentiating permanent from temporary wet strength, permanent will be defined as those resins which, when incorporated into paper or tissue products, will provide a product that retains more than 50% of its original wet strength after exposure to water for a period of at least five minutes. Temporary wet strength agents are those which show less than 50% of their original wet strength after exposure to water for five minutes. Both classes of material find application in the present invention. The amount of wet strength agent added to the pulp fibers can be at least about 0.1 dry weight percent, more specifically about 0.2 dry weight percent or greater, and still more specifically from about 0.1 to about 3 dry weight percent based on the dry weight of the fibers.

Permanent wet strength agents will provide a more or less long-term wet resilience to the structure. This type of structure would find application in products that would require long-term wet resilience such as in paper towels and in many absorbent consumer products. In contrast, the temporary wet strength agents would provide structures that had low density and high resilience, but would not provide a structure that had long-term resistance to exposure to water or body fluids. While the structure would have good integrity initially, after a period of time the structure would begin to lose its wet resilience. This property can be used to some advantage in providing materials that are highly absorbent when initially wet, but which after a period of time lose their integrity. This property could be used in providing "flushable" products. The mechanism by which the wet strength is generated has little influence on the products of this invention as long as the essential property of generating water-resistant bonding at the fiber/fiber bond points is obtained.

The permanent wet strength agents that are of utility in the present invention are typically water soluble, cationic oligomeric or polymeric resins that are capable of either crosslinking with themselves (homocrosslinking) or with the cellulose or other constituent of the wood fiber. The most widely-used materials for this purpose are the class of polymer known as polyamide-polyamine-epichlorohydrin (PAE) type resins. These materials have been described in patents issued to Keim (U.S. Pat. Nos. 3,700,623 and 3,772,076) and are sold by Hercules, Inc., Wilmington, Del., as Kymene 557H. Related materials are marketed by Henkel Chemical Co., Charlotte, N.C. and Georgia-Pacific Resins, Inc., Atlanta, Ga.

Polyamide-epichlorohydrin resins are also useful as bonding resins in this invention. Materials developed by Monsanto and marketed under the Santo Res label are base-activated polyamide-epichlorohydrin resins that can be used in the present invention. These materials are described in patents issued to Petrovich (U.S. Pat. Nos. 3,885,158; 3,899, 388; 4,129,528 and 4,147,586) and van Eenam (U.S. Pat. No. 4,222,921). Although they are not as commonly used in consumer products, polyethylenimine resins are also suitable for immobilizing the bond points in the products of this invention. Another class of permanent-type wet strength agents are exemplified by the aminoplast resins obtained by reaction of formaldehyde with melamine or urea.

The temporary wet strength resins that can be used in connection with this invention include, but are not limited to, those resins that have been developed by American Cyanamid and are marketed under the name Parez 631 NC (now available from Cytec Industries, West Paterson, N.J.). This and similar resins are described in U.S. Pat. No. 3,556,932 to Coscia et al. and U.S. Pat. No. 3,556,933 to Williams et al. Other temporary wet strength agents that should find application in this invention include modified starches such as those available from National Starch and marketed as Co-Bond 1000. It is believed that these and related starches are covered by U.S. Pat. No. 4,675,394 to Solarek et al. Derivatized dialdehyde starches, such as described in Japanese Kokai Tokkyo Koho JP 03,185,197, should also find application as useful materials for providing temporary wet strength. It is also expected that other temporary wet strength materials such as those described in U.S. Pat. Nos. 4,981,557; 5,008,344 and 5,085,736 to Bjorkquist would be of use in this invention. With respect to the classes and the types of wet strength resins listed, it should be understood that this listing is simply to provide examples and that this is neither meant to exclude other types of wet strength resins, nor is it meant to limit the scope of this invention.

Although wet strength agents as described above find particular advantage for use in connection with in this invention, other types of bonding agents can also be used to provide the necessary wet resiliency. They can be applied at the wet end or applied by spraying or printing, etc. after the web is formed or after it is dried.

As used herein, the "wet:dry ratio" is the ratio of the geometric mean wet tensile strength divided by the geometric mean dry tensile strength. Geometric mean tensile strength (GMT) is the square root of the product of the machine direction tensile strength and the cross-machine direction tensile strength of the web. Unless otherwise indicated, the term "tensile strength" means "geometric mean tensile strength." The webs of this invention have a wet:dry ratio of about 0.1 or greater, more specifically about 0.15 or greater, more specifically about 0.2 or greater, still more specifically about 0.3 or greater, still more specifically about 0.4 or greater, and still more specifically from about 0.2 to about 0.6. Tensile strengths can be measured using an Instron tensile tester using a 3 inches jaw width, a jaw span of 4 inches, and a crosshead speed of 10 inches per minute after maintaining the sample under TAPPI conditions for 4 hours before testing. The webs of this invention also preferably have a minimum absolute ratio of dry tensile strength to basis weight of 10 grams/gsm, preferably 15 grams/gsm, more preferably 20 grams/gsm, more preferably 30 grams/gsm, and still more preferably 40 grams/gsm and preferably from about 20 to about 100 grams/gsm. The webs of this invention also preferably have a minimum absolute ratio of wet tensile strength to basis weight of about 1 gram/gsm, preferably about 2 grams/gsm, more preferably about 5 grams/gsm, more preferably about 10 grams/gsm and still more preferably about 20 grams/gsm and preferably from about 15 to about 50 grams/gsm.

"Overall Surface Depth". A three-dimensional basesheet or web is a sheet with significant variation in surface elevation due to the intrinsic structure of the sheet itself. As used herein, this elevation difference is expressed as the "Overall Surface Depth." The webs of this invention possess three-dimensionality and have an Overall Surface Depth of about 0.1 mm. or greater, more specifically about 0.3 mm. or greater, still more specifically about 0.4 mm. or greater, still more specifically about 0.5 mm. or greater, and still more specifically from about 0.4 to about 0.8 mm.

The three-dimensional structure of a largely planar sheet can be described in terms of its surface topography. Rather than presenting a nearly flat surface, as is typical of conventional paper, the molded sheets of the present invention have significant topographical structures that derive in part from the use of sculptured through-drying fabrics such as those taught by Chiu et al. in U.S. Pat. No. 5,429,686, "Apparatus for Making Soft Tissue Products," issued Jul. 4, 1995, which is hereby incorporated by reference. The resulting paper surface topography typically comprises a regular repeating unit cell that is typically a parallelogram with sides between 2 and 20 mm in length. It is important that these three-dimensional structures be created by molding the moist sheet or be created prior to drying, rather than by creping or embossing or other operations after the sheet has been dried. In this manner, the three-dimensional structure is more likely to be well-retained upon wetting, helping to provide high wet resiliency and to promote good in-plane permeability.

In addition to the regular geometrical structure imparted by the sculptured fabrics and other fabrics used in creating a sheet, additional fine structure, with an in-plane length scale less than about 1 mm, can be present in the sheet. Such a fine structure can stem from microfolds created during differential velocity transfer of the web from one fabric or wire to another prior to drying. Some of the materials of the present invention, for example, appear to have fine structure with a fine surface depth of 0.1 mm or greater, and sometimes 0.2 mm or greater, when height profiles are measured using a commercial moiré interferometer system. These fine peaks have a typical half-width less than 1 mm. The fine structure from differential velocity transfer and other treatments may be useful in providing additional softness, flexibility, and bulk. Measurement of the surface structures is described below.

An especially suitable method for measurement of Overall Surface Depth is moiré interferometry, which permits accurate measurement without deformation of the surface. For reference to the materials of the present invention, surface topography should be measured using a computer-controlled white-light field-shifted moiré interferometer with about a 38 mm field of view. The principles of a useful implementation of such a system are described in Bieman et al. (L. Bieman, K. Harding, and A. Boehnlein, "Absolute Measurement Using Field-Shifted Moiré," SPIE Optical Conference Proceedings, Vol. 1614, pp. 259–264, 1991). A suitable commercial instrument for moiré interferometry is the CADEYES® interferometer produced by Medar, Inc. (Farmington Hills, Mich.), constructed for a 38-mm field-of-view (a field of view within the range of 37 to 39.5 mm is adequate). The CADEYES® system uses white light which is projected through a diffraction grid to project fine black lines onto the sample surface. The surface is viewed through a similar diffraction grid, creating moiré fringes that are viewed by a CCD camera. Suitable lenses and a stepper motor adjust the optical configuration for field shifting (a technique described below). A video processor sends captured fringe images to a PC computer for processing, allowing details of surface height to be back-calculated from the fringe patterns viewed by the video camera.

In the CADEYES moiré interferometry system, each pixel in the CCD video image is said to belong to a moiré fringe that is associated with a particular height range. The method of field-shifting, as described by Bieman et al. (L. Bieman, K. Harding, and A. Boehnlein, "Absolute Measurement Using Field-Shifted Moiré," SPIE Optical Conference Proceedings, Vol. 1614, pp. 259–264,1991) and as originally patented by Boehnlein (U.S. Pat. No. 5,069,548, herein incorporated by reference), is used to identify the fringe number for-each point in the video image (indicating which fringe a point belongs to). The fringe number is needed to determine the absolute height at the measurement point relative to a reference plane. A field-shifting technique (sometimes termed phase-shifting in the art) is also used for sub-fringe analysis (accurate determination of the height of the measurement point within the height range occupied by its fringe). These field-shifting methods coupled with a camera-based interferometry approach allows accurate and rapid absolute height measurement, permitting measurement to be made in spite of possible height discontinuities in the surface. The technique allows absolute height of each of the roughly 250,000 discrete points (pixels) on the sample surface to be obtained, if suitable optics, video hardware, data acquisition equipment, and software are used that incorporates the principles of moiré interferometry with field-shifting. Each point measured has a resolution of approximately 1.5 microns in its height measurement.

The computerized interferometer system is used to acquire topographical data and then to generate a grayscale image of the topographical data, said image to be hereinafter called "the height map." The height map is displayed on a computer monitor, typically in 256 shades of gray and is quantitatively based on the topographical data obtained for the sample being measured. The resulting height map for the 38-mm square measurement area should contain approximately 250,000 data points corresponding to approximately 500 pixels in both the horizontal and vertical directions of the displayed height map. The pixel dimensions of the height map are based on a 512×512 CCD camera which provides images of moiré patterns on the sample which can be analyzed by computer software. Each pixel in the height map represents a height measurement at the corresponding x- and y-location on the sample. In the recommended system, each pixel has a width of approximately 70 microns, i.e. represents a region on the sample surface about 70 microns long in both orthogonal in-plane directions). This level of resolution prevents single fibers projecting above the surface from having a significant effect on the surface height measurement. The z-direction height measurement must have a nominal accuracy of less than 2 microns and a z-direction range of at least 1.5 mm. (For further background on the measurement method, see the CADEYES Product Guide, Medar, Inc., Farmington Hills, Mich., 1994, or other CADEYES manuals and publications of Medar, Inc.)

The CADEYES system can measure up to 8 moiré fringes, with each fringe being divided into 256 depth counts (sub-fringe height increments, the smallest resolvable height difference). There will be 2048 height counts over the measurement range. This determines the total z-direction range, which is approximately 3 mm in the 38-mm field-of-view instrument. If the height variation in the field of view covers more than eight fringes, a wrap-around effect occurs, in which the ninth fringe is labeled as if it were the first fringe and the tenth fringe is labeled as the second, etc. In other words, the measured height will be shifted by 2048 depth counts. Accurate measurement is limited to the main field of 8 fringes.

The moiré interferometer system, once installed and factory calibrated to provide the accuracy and z-direction range stated above, can provide accurate topographical data for materials such as paper towels. (Those skilled in the art may confirm the accuracy of factory calibration by performing measurements on surfaces with known dimensions.) Tests are performed in a room under Tappi conditions (73° F., 50% relative humidity). The sample must be placed flat on a surface lying aligned or nearly aligned with the measurement plane of the instrument and should be at such a height that both the lowest and highest regions of interest are within the measurement region of the instrument.

Once properly placed, data acquisition is initiated using Medar's PC software and a height map of 250,000 data points is acquired and displayed, typically within 30 seconds from the time data acquisition was initiated. (Using the CADEYES® system, the "contrast threshold level" for noise rejection is set to 1, providing some noise rejection without excessive rejection of data points.) Data reduction and display are achieved using CADEYES® software for PCs, which incorporates a customizable interface based on Microsoft Visual Basic Professional for Windows (version 3.0). The Visual Basic interface allows users to add custom analysis tools.

The height map of the topographical data can then be used by those skilled in the art to identify characteristic unit cell structures (in the case of structures created by fabric patterns; these are typically parallelograms arranged like tiles to cover a larger two-dimensional area) and to measure the typical peak to valley depth of such structures. A simple method of doing this is to extract two-dimensional height profiles from lines drawn on the topographical height map which pass through the highest and lowest areas of the unit cells. These height profiles can then be analyzed for the peak to valley distance, if the profiles are taken from a sheet or portion of the sheet that was lying relatively flat when measured. To eliminate the effect of occasional optical noise and possible outliers, the highest 10% and the lowest 10% of the profile should be excluded, and the height range of the remaining points is taken as the surface depth. Technically, the procedure requires calculating the variable which we term "P10," defined at the height difference between the 10% and 90% material lines, with the concept of material lines being well known in the art, as explained by L. Mummery, in *Surface Texture Analysis: The Handbook*, Hommelwerke GmbH, Mühlhausen, Germany, 1990. In this approach, the surface is viewed as a transition from air to material. For a given profile, taken from a flat-lying sheet, the greatest height at which the surface begins—the height of the highest peak—is the elevation of the "0% reference line" or the "0% material line," meaning that 0% of the length of the horizontal line at that height is occupied by material. Along the horizontal line passing through the lowest point of the profile, 100% of the line is occupied by material, making that line the "100% material line." In between the 0% and 100% material lines (between the maximum and minimum points of the profile), the fraction of horizontal line length occupied by material will increase monotonically as the line elevation is decreased. The material ratio curve gives the relationship between material fraction along a horizontal line passing through the profile and the height of the line; this relationship is sketched in FIG. 2. The material ratio curve is also the cumulative height distribution of a profile. (A more accurate term might be "material fraction curve.")

Once the material ratio curve is established, one can use it to define a characteristic peak height of the profile. The P10 "typical peak-to-valley height" parameter is defined as the difference between the heights of the 10% and 90% material lines. This parameter is relatively robust in that outliers or unusual excursions from the typical profile structure have little influence on the P10 height. The units of P10 are mm. The Overall Surface Depth of a material is reported as the P10 surface depth value for profile lines encompassing the height extremes of the typical unit cell of that surface. "Fine surface depth" is the P10 value for a profile taken along a plateau region of the surface which is relatively uniform in height relative to profiles encompassing a maxima and minima of the unit cells. Measurements are reported for the most textured side of the materials of the present invention, which is typically the side that was in contact with the through-drying fabric when air flow is toward the through-dryer. FIGS. 3A, 3B and 3C show typical profiles from a sample of SURPASS, which is a commercial uncreped, through-dried material made with secondary fibers. The Overall Surface Depth is seen to be about 0.3 mm. Typical fine elements have a fine surface depth less than 0.15 mm. FIGS. 4A, 4B and 4C present profiles from Sample U2 of the present invention, described hereafter in the Examples. The Overall Surface Depth is over 0. 4 mm, and the fine structure has a surface depth of about 0.3 mm. FIG. 5 represents a profile of Sample U8 of the present invention, having an Overall Surface Depth of about 0.5 mm.

Overall Surface Depth is intended to examine the topography produced in the basesheet, especially those features created in the sheet prior to and during drying processes, but is intended to exclude "artificially" created large-scale topography from dry converting operations such as embossing, perforating, pleating, etc. Therefore, the profiles examined should be taken from unembossed regions if the sheet has been embossed, or should be measured on an unembossed sheet. Overall Surface Depth measurements should exclude large-scale structures such as pleats or folds which do not reflect the three-dimensional nature of the original basesheet itself. It is recognized that sheet topography may be reduced by calendering and other operations which affect the entire basesheet. Overall Surface Depth measurement can be appropriately performed on a calendered sheet.

The Wet Wrinkle Recovery Test" is used to quantify wet bending resiliency. It is a slight modification of AATCC Test Method 66-1990 taken from the Technical Manual of the American Association of Textile Chemists and Colorists (1992), page 99. The modification is to first wet the samples before carrying out the method. This is done by soaking the samples in water containing 0.01 percent TRITON X-100 wetting agent (Rohm & Haas) for five minutes before testing. Sample preparation is carried out at 73° F. and 50 percent relative humidity. The sample is gently removed from the water with a tweezers, drained by pressing between two pieces of blotter paper with 325 grams of weight, and placed in the sample holder to be tested as with the dry wrinkle recovery test method. The test measures the highest recovery angle of the sample being tested (in any direction, including the machine direction and the cross-machine direction), with 180° representing total recovery. The Wet Wrinkle Recovery, expressed as a percent recovery, is the measured recovery angle divided by 180°, multiplied by 100. Absorbent structures of this invention can exhibit a Wet Wrinkle Recovery of about 60 percent or greater, more specifically about 70 percent or greater, and still more specifically about 80 percent or greater.

"Wet compressive resiliency" of the new materials is defined by several parameters and can be demonstrated using a materials property procedure that encompasses both wet and dry characteristics. A programmable strength measurement device is used in compression mode to impart a specified series of compression cycles to an initially dry, conditioned sample, after which the sample is carefully moistened in a specified manner and subjected to the same sequence of compression cycles. While the comparison of wet and dry properties is of general interest, the most important information from this test concerns the wet properties. The initial testing of the dry sample can be viewed as a conditioning step. The test sequence begins with compression of the dry sample to 0.025 psi to obtain an initial thickness (cycle A), then two repetitions of loading up to 2 psi followed by unloading (cycles B and C). Finally, the sample is again compressed to 0.025 psi to obtain a final thickness (cycle D). (Details of the procedure, including compression speeds, are given below). Following the treatment of the dry sample, moisture is applied uniformly to the sample using a fine mist of deionized water to bring the moisture ratio (g water/g dry fiber) to approximately 1.1. This is done by applying 95–110% added moisture, based on the conditioned sample mass. This puts typical cellulosic materials in a moisture range where physical properties are relatively insensitive to moisture content (e.g., the sensitivity is much less than it is for moisture ratios less than 70%). The moistened sample is then placed in the test device and the compression cycles are repeated.

Three measures of wet resiliency are considered which are relatively insensitive to the number of sample layers used in the stack. The first measure is the bulk of the wet sample at 2 psi. This is referred to as the "Wet Compressed Bulk" (WCB). The second measure is termed "Wet Springback Ratio (WS)", which is the ratio of the moist sample thickness at 0.025 psi at the end of the compression test (cycle D) to the thickness of the moist sample at 0.025 psi measured at the beginning of the test (cycle A). The third measure is the "Loading Energy Ratio" (LER), which is the ratio of loading energy in the second compression to 2 psi (cycle C) to that of the first compression to 2 psi (cycle B) during the sequence described above, for a wetted sample. The final wet bulk measured at the end of the test (at 0.025 psi) is termed the "final bulk" or "FB" value. When load is plotted as a function of thickness, loading energy is the area under the curve as the sample goes from an unloaded state to the peak load of that cycle. For a purely elastic material, the springback and loading energy ratio would be unity. We have found that the three measures described here are relatively independent of the number of layers in the stack and serve as useful measures of wet resiliency. Also referred to herein is the "Compression Ratio", which is defined as the ratio of moistened sample thickness at peak load in the first compression cycle to 2 psi to the initial moistened thickness at 0.025 psi.

In carrying out the foregoing measurements of the wet compressive resiliency, samples should be conditioned for at least 24 hours under TAPPI conditions (50% RH, 73° F.). Specimens are die cut to 2.5"×2.5" squares. Conditioned sample weight should be near 0.4 g, if possible, and within the range of 0.25 to 0.6 g for meaningful comparisons. The target mass of 0.4 to 0.5 gram is achieved by using a stack of 2 or more sheets if the sheet basis weight is less than 65 gsm. For example, for nominal 30 gsm sheets, a stack of 3 sheets will generally be near 0.4 g total mass. Three sheets are preferred for 40 gsm sheets, while 2 sheets should be used for 60 gsm sheets.

Compression measurements are performed using an Instron 4502 Universal Testing Machine interfaced with a 286 PC computer running Instron Series XII software (1989 issue) and Version 2 firmware. The standard "286 computer" referred to has an 80286 processor with a 12 MHz clock speed. The particular computer used was a Compaq DeskPro 286e with an 80287 math coprocessor and a VGA video adapter. A 1 kN load cell is used with 2.25" diameter circular platens for sample compression. The lower platen has a ball bearing assembly to allow exact alignment of the platens. The lower platen is locked in place while under load (30–100 lbf) by the upper platen to ensure parallel surfaces. The upper platen must also be locked in place with the standard ring nut to eliminate play in the upper platen as load is applied.

Following at least one hour of warm-up after start-up, the instrument control panel is used to set the extensionometer to zero distance while the platens are in contact (at a load of 10–30 lb). With the upper platen freely suspended, the calibrated load cell is balanced to give a zero reading. The extensionometer and load cell should be periodically checked to prevent baseline drift (shirting of the zero points). Measurements must be performed in a controlled humidity and temperature environment, according to TAPPI specifications (50%±2% rh and 73° F.). The upper platen is then raised to a height of 0.2 in. and control of the Instron is transferred to the computer.

Using the Instron Series XII Cyclic Test software with a 286 computer, an instrument sequence is established with 7 markers (discrete events) composed of 3 cyclic blocks (instructions sets) in the following order:

Marker 1: Block 1
Marker 2: Block 2
Marker 3: Block 3
Marker 4: Block 2
Marker 5: Block 3
Marker 6: Block 1
Marker 7: Block 3.

Block 1 instructs the crosshead to descend at 1.5 in./min. until a load of 0.1 lb. is applied (the Instron setting is −0.1 lb., since compression is defined as negative force). Control is by displacement. When the targeted load is reached, the applied load is reduced to zero.

Block 2 directs that the crosshead range from an applied load of 0.05 lb. to a peak of 8 lb. then back to 0.05 lb. at a speed of 0.4 in./min. Using the Instron software, the control mode is displacement, the limit type is load, the first level is −0.05 lb., the second level is −8 lb., the dwell time is 0 sec., and the number of transitions is 2 (compression, then relaxation); "no action" is specified for the end of the block.

Block 3 uses displacement control and limit type to simply raise the crosshead to 0.2 in. at a speed of 4 in./min., with 0 dwell time. Other Instron software settings are 0 in first level, 0.2 in second level, 1 transition, and "no action" at the end of the block.

When executed in the order given above (Markers 1–7), the Instron sequence compresses the sample to 0.025 psi (0.1 lbf), relaxes, then compresses to 2 psi (8 lbs.), followed by decompression and a crosshead rise to 0.2 in., then compress the sample again to 2 psi, relaxes, lifts the crosshead to 0.2 in., compresses again to 0.025 psi (0.1 lbf), and then raises the crosshead. Data logging should be performed at intervals no greater than every 0.02" or 0.4 lb. (whichever comes first) for Block 2 and for intervals no greater than 0.01 lb. for Block 1. Preferably, data logging is performed every 0.004 lb. in Block 1 and every 0.05 lb. or 0.005 in. (whichever comes first) in Block 2.

The results output of the Series XII software is set to provide extension (thickness) at peak loads for Markers 1, 2, 4 and 6 (at each 0.025 and 2.0 psi peak load), the loading energy for Markers 2 and 4 (the two compressions to 2.0 psi previously termed cycles B and C, respectively), the ratio of the two loading energies (second cycle/first cycle), and the ratio of final thickness to initial thickness (ratio of thickness at last to first 0.025 psi compression). Load versus thickness results are plotted on the screen during execution of Blocks 1 and 2.

In performing a measurement, the dry, conditioned sample is centered on the lower platen and the test is initiated. Following completion of the sequence, the sample is immediately removed and moisture (deionized water at 72–73° F.) is applied. Moisture is applied uniformly with a fine mist to reach a moist sample mass of approximately 2.0 times the initial sample mass (95–110% added moisture is applied, preferably 100% added moisture, based on conditioned sample mass; this level of moisture should yield an absolute moisture ratio of about 1.1 g. water/g. oven dry fiber—with oven dry referring to drying for at least 30 minutes in an oven at 105° C.). (For the uncreped through-dried materials of this invention, the moisture ratio could be within the range of 1.05 to 1.7 without significantly affecting the results). The mist should be applied uniformly to separated sheets (for stacks of more than 1 sheet), with spray applied to both front and back of each sheet to ensure uniform moisture application. This can be achieved using a conventional plastic spray bottle, with a container or other barrier blocking most of the spray, allowing only about the upper 10–20% of the spray envelope—a fine mist—to approach the sample. The spray source should be at least 10" away from the sample during spray application. In general, care must be applied to ensure that the sample is uniformly moistened by a fine spray. The sample must be weighed several times during the process of applying moisture to reach the targeted moisture content. No more than three minutes should elapse between the completion of the compression test on the dry sample and the completion of moisture application. Allow 45–60 seconds from the final application of spray to the beginning of the subsequent compression test to provide time for internal wicking and absorption of the spray. Between three and four minutes will elapse between the completion of the dry compression sequence and initiation of the wet compression sequence.

Once the desired mass range has been reached, as indicated by a digital balance, the sample is centered on the lower Instron platen and the test sequence is initiated. Following the measurement, the sample is placed in a 105° C. oven for drying, and the oven dry weight will be recorded later (sample should be allowed to dry for 30–60 minutes, after which the dry weight is measured).

Note that creep recovery can occur between the two compression cycles to 2 psi, so the time between the cycles may be important. For the instrument settings used in these Instron tests, there is roughly a 30 second period (typically ±4 sec.) between the beginning of compression during the two cycles to 2 psi. The beginning of compression is defined as the point at which the load cell reading exceeds 0.03 lb. Likewise, there is a 5–8 second interval between the beginning of compression in the first thickness measurement (ramp to 0.025 psi) and the beginning of the subsequent compression cycle to 2 psi. The interval between the beginning of the second compression cycle to 2 psi and the beginning of compression for the final thickness measurement is approximately 20 seconds.

The utility of a web or absorbent structure having a high Wet Compressed Bulk (WCB) value is obvious, for a wet material which can maintain high bulk under compression can maintain higher fluid capacity and is less likely to allow fluid to be squeezed out when it is compressed.

High Wet Springback Ratio values are especially desirable because a wet material that springs back after compression can maintain high pore volume for effective intake and distribution of subsequent insults of fluid, and such a material can regain fluid during its expansion which may have been expelled during compression. In diapers, for example, a wet region may be momentarily compressed by body motion or changes in body position. If the material is unable to regain its bulk when the compressive force is released, its effectiveness for handling fluid is reduced.

High Loading Energy Ratio values in a material are also useful, for such a material continues to resist compression (LER is based on a measure of the energy required to compress a sample) at loads less than the peak load of 2 psi, even after it has been heavily compressed once. Maintaining such wet elastic properties is believed to contribute to the feel of the material when used in absorbent articles, and may help maintain the fit of the absorbent article against the wearer's body, in addition to the general advantages accrued when a structure can maintain its pore volume when wet.

The webs of this invention can exhibit one or more of the foregoing properties. More specifically, the webs of this invention can have a Wet Compressed Bulk of about 6 cubic centimeters per gram or greater, more specifically about 7 cubic centimeters per gram or greater, more specifically about 8 cubic centimeters per gram or greater, and still more specifically from about 8 to about 13 cubic centimeters per gram. The Compression Ratio can be about 0.7 or less, more specifically about 0.6 or less, still more specifically about 0.5 or less, and still more specifically from 0.4 to about 0.7. Also, they can have a Wet Springback Ratio of about 0.75 or greater, more specifically about 0.85 or greater, more specifically about 0.90 or greater, and still more specifically from about 0.8 to about 0.93. The Loading Energy Ratio can be about 0.7 or greater, more specifically about 0.8 or greater, and still more specifically from about 0.7 to about 0.9.

"In-Plane Permeability". An important property of porous media, particularly for absorbent products, is the permeability to liquid flow. The complex, interconnected pathways between the solid particles and boundaries of a porous media provide routes for fluid flow which may offer significant flow resistance due to the narrowness of the channels and the tortuosity of the pathways.

For paper, permeability is commonly expressed in terms of gas flow rates through a sheet. This practice is useful for comparing similar sheets, but does not truly characterize the interaction of flowing fluid with the porous structure and provides no direct information about flow in a wet sheet. The standard engineering definition of permeability provides a more useful parameter, though one less easily measured. The standard definition is based on Darcy's law (see F. A. L. Dullien, *Porous Media: Fluid Transport and Pore Structure*, Academic Press, New York, 1979), which, for one-dimensional flow, states that the velocity of fluid flow through a saturated porous medium is directly proportional to the pressure gradient:

$$V = \frac{K}{\mu} \frac{\Delta P}{L} \tag{1}$$

where V is the superficial velocity (flow rate divided by area), K is the permeability, $\mu$ is the fluid viscosity, and $\Delta P$ is the pressure drop in the flow direction across a distance L. The units of K are $m^2$. In Equation (1), the permeability is an empirical proportionality parameter linking fluid velocity to pressure drop and viscosity. For a homogeneous medium, K is not a function of $\Delta P$, sample length, or viscosity, but is an intrinsic parameter describing the flow resistance of the medium. In a compressible medium, permeability will be a function of the degree of compression. Darcian permeability is a fundamental parameter for processes involving fluid flow in fibrous webs.

Darcian permeability has units of area ($m^2$) and for simple uniform cylindrical pores is proportional to the cross sectional area of a single pore. However, the permeability of most real materials cannot be predicted from an optical assessment of pore size. Permeability is determined not only by pore size, but also pore orientation, tortuosity, and interconnectedness. Large pores in the body of an object may be inaccessible to fluid flow or accessible only through minute pores offering high flow resistance. Even with a full three-dimensional description of the pore space of a material from x-ray tomography or other imaging techniques, it is difficult to predict or calculate the permeability. Permeability and pore size determinations are related but distinct pieces of information about a material. For example, a sheet of metal with discreet, nonoverlapping holes punched in it may have very large pores (the holes), while still having negligible In-Plane Permeability. Swiss cheese has many large pores, but typically has negligible permeability in any direction unless sliced so thin that individual holes can extend from one face to the other of the cheese sample.

Most studies of permeability in paper have focused on flow in the z-direction (normal to the plane of the sheet), which is of practical importance in wet pressing and other unit operations. However, paper is an anisotropic material (for example, see E. L. Back, "The Pore Anisotropy of Paper Products and Fibre Building Boards," Svensk Papperstidning, 69: 219 (1966)), meaning that fluid flow properties are a function of direction. In this case, different flow directions will appear to have different apparent permeabilities. The many possibilities of flow direction and pressure gradients in such a medium can be encompassed with a multidimensional form of Darcy's law, $$\overline{v} = \frac{-\overline{\overline{K}} \cdot \nabla P}{\mu}, \tag{2}$$

where $\overline{v}$ is the superficial velocity vector (volumetric flow rate divided by cross-sectional area of the flow), $\mu$ is the viscosity of the fluid, $\overline{\overline{K}}$ is a second-order tensor and $\nabla P$ is the pressure gradient. If a Cartesian coordinate system is chosen to correspond with the principal flow directions of the porous medium, then the permeability tensor becomes a diagonal matrix (see Jacob Bear, "Dynamics of Fluids in Porous Media.," American Elsevier, New York, N.Y., 1972, pp. 136–151):

$$\overline{\overline{K}} = \begin{bmatrix} K_x & 0 & 0 \\ 0 & K_y & 0 \\ 0 & 0 & K_z \end{bmatrix}, \quad (3)$$

where $K_x$, $K_y$, and $K_z$ are the principal permeability components in the x-, y-, and z-directions, respectively. In paper, these directions will generally correspond to the cross-direction (taken here as y) and the machine-direction (taken as x, the direction of maximum In-Plane Permeability) in the plane, and the transverse or thickness direction (z). Thus, the anisotropic permeability of typical machine-made paper can be characterized with three permeability parameters, one for the machine-direction, one for the cross-direction, and one for the z-direction. (In some cases, as when there are unbalanced flows in the headbox of the paper machine, the direction of maximum permeability may be slightly off from the machine direction; the direction of maximum In-Plane Permeability and the direction orthogonal to that should be used for the x- and y-directions, respectively, in that case.) In handsheets, there may be no preferential direction of orientation for fibers lying in the plane, so the x- and y-direction permeability values should be equal (in other words, such a sheet is isotropic in the plane).

In spite of the past focus on z-direction permeability in paper, In-Plane Permeability (both $K_x$ and $K_y$ are in-plane factors) is important in a variety of applications, especially in absorbent articles. Body fluids or other liquids flowing into the absorbent article usually enter the article in a narrow, localized region. Efficient use of the absorbent medium requires that the incoming fluid be distributed laterally through in-plane flow in the absorbent article, otherwise the local capacity of the article to handle the incoming liquid may be overwhelmed resulting in leakage and poor utilization of the absorbent core. The ability of fluid to flow in the plane of the article is a function of the driving force for fluid flow, which can be a combination of capillary wicking and hydraulic pressure from fluid source, and of the ability of the porous medium to conduct flow, which is described in large part by the Darcian permeability of the material. Two-phase flow and non-Newtonian liquids or suspensions complicate the physics, but the in-plane permeability of the porous medium is a critical factor for rapid in-plane distribution of liquid insults. Especially in the case of urine management, where liquid flow rates may occur far in excess of the ability of capillary forces, high In-Plane Permeability is needed in the intake layer to allow the fluid to be distributed laterally rather than to leak.

While many past studies of liquid permeability in paper focused exclusively on measuring $K_z$ for z-direction flow, more recently, methods have been taught for measuring permeability in the plane of a paper sheet. J. D. Lindsay and P. H. Brady teach methods for in-plane and z-direction permeability measurements of saturated paper in "Studies of Anisotropic Permeability with Applications to Water Removal in Fibrous Webs: Part I," Tappi J., 76(9): 119–127 (1993) and "Studies of Anisotropic Permeability with Applications to Water Removal in Fibrous Webs: Part II," Tappi J., 76(11): 167–174 (1993). Related methods have been published by K. L. Adams, B. Miller, and L. Rebenfeld in "Forced In-Plane Flow of an Epoxy Resin in Fibrous Networks," Polymer Engineering and Science, 26(20): 1434–1441 (1986); J. D. Lindsay in "Relative Flow Porosity in Fibrous Media: Measurements and Analysis, Including Dispersion Effects," Tappi J., 77(6): 225–239 (June 1994); J. D. Lindsay and J. R. Wallin, "Characterization of In-Plane Flow in Paper," AIChE 1989 and 1990 Forest Products Symposium, Tappi Press, Atlanta, Ga. (1992), p. 121; and D. H. Horstmann, J. D. Lindsay, and R. A. Stratton, "Using Edge-Flow Tests to Examine the In-Plane Anisotropic Permeability of Paper," Tappi J., 74(4): 241 (1991).

The basic method used in most of these publications is injection of fluid into the center of a paper disk that is constrained between two flat surfaces to force the fluid flow to be in the radial direction, proceeding from the injection point at the center of the disk to the outer edge of the disk. This is illustrated in FIG. 6, which depicts a sheet in which a central hole has been punched and into which fluid is injected by means of an injection port of the same size as the punched hole. For a liquid-saturated sheet of constant thickness subject to steady radial fluid flow in the manner described in the work of Lindsay and others, the equation relating average In-Plane Permeability to fluid flow is:

$$K_r \equiv \frac{K_x + K_y}{2} = \frac{Q\mu \ln(R_o/R_i)}{2\pi L_p \Delta P}, \quad (4)$$

where $R_o$ is the radius of the paper disk, $R_i$ is the radius of the central hole in the sample into which fluid is injected through an injection port; $L_P$ is the thickness of the paper; $\Delta P$ is the constant pressure above atmospheric pressure at which fluid is injected into the disk (the gauge pressure at the injection pore); Q is the volumetric flow rate of liquid, and $K_r$ is the In-Plane Permeability, technically the average radial permeability, defined as the average of the two in-plane permeability components.

Details of the disk geometry used in the experimental work are shown in FIG. 7. The disk diameter is typically 5 inches, although in some cases, the maximum available sample size was 4.5 inches. The central inlet hole was consistently 0.375 inches (⅜ inch) and was created using a paper punch tool. The test apparatus for In-Plane Permeability measurements is depicted in FIGS. 8 and 9, which is identical in principle to the apparatus taught by Lindsay and Brady (op. cit.). Tubing connects water from a water reservoir to an injection port drilled into a 1-inch thick Plexiglas support plate. (The support plate is transparent to permit viewing of the wetted sample, especially in cases when an aqueous dye solution is injected into the sample. A mirror at a 45 degree angle below the support plate facilitates viewing and photography.) The water reservoir provides a nearly constant hydraulic head for fluid injection during the test. The volumetric flow rate is obtained by noting the change in water reservoir mass as a function of time, and converting the water mass flow rate to a volumetric flow rate. Vacuum-deaerated deionized water at room temperature is used.

In the apparatus of FIG. 8, a paper disk, cut to the dimensions shown in FIG. 7 (5-inch diameter and 0.375-inch central hole), is placed over the injection port (0.375 inches diameter also) and is then saturated with water. The fluid injection line and the injection port should be filled with water and efforts should be taken to avoid air bubbles being trapped in the sheet or in the injection area. To help eliminate air pockets, the sample should be bent gently in the center as it is placed on the wet support plate to initiate liquid contact in the center of the sample; the edges can then be lowered gradually to create a wedge-like motion of the liquid meniscus to sweep air bubbles out from under the sheet. Multi-ply stacks of sheets can be handled in the same way, although preliminary sample wetting may be needed to remove interply air bubbles. The goal in removing air bubbles is to reduce the flow blockage that trapped air bubbles can cause.

Once the wetted sample is in place, a cylindrical metal platen, 5-inches in diameter, is gently lowered on top of the sample to provide a constant compressive load and to provide a reference surface on its top for thickness measurement with displacement gauges. Three displacement gauges are used, spaced approximately evenly around the edge of the top of the metal cylinder, in order to measure the average thickness of the sheet. The sample thickness is taken as the average of the three displacement values relative to a zero point when no sample is present. A suitable thickness gauge is the Mitutoyo Digimatic Indicator, Model 543–525–1, with a 2-inch stroke (traveling distance of the contacting spindle) and a precision of 1 micrometer. The thickness gauges are rigidly mounted relative to the support plate. The contacting spindles of the thickness gauges can be raised and lowered (without changing the position of the body of the gauge) by use of a cable to provide clearance for moving the metal platen onto the sample. The small force applied by the thickness gauges should be added to the weight of the metal platen to obtain the total force applied to the sample; this force, when divided by the cross sectional area of the sample and platen, should be 0.8 psi.

A hydraulic head of 13 inches is used to drive the liquid flow. This head is achieved by placement of a water bottle, filled to a specified level, on a mass balance at a fixed height relative to the support plate on which the sample rests. As the sample is being placed on the support plate, the water reservoir is at such a height that the water level in the reservoir is nearly the same as (or slightly greater than) the support plate on which the sample rests. When the sample has been moistened and placed under the compressive load of the metal platen, the water reservoir is then raised and placed on a mass balance such that the water level is 13 inches above the support platen. A timer is activated and the water reservoir mass is recorded at 20 seconds or 30 seconds intervals for a least 90 seconds. The thickness readings of the three gauges is also recorded regularly during the test. To reduce creep, the saturated sample should be allowed to equilibrate under the compressive load for at least 30 seconds before the water bottle is raised and forced flow through the sample begins.

The change in water reservoir mass as a function of time gives the mass flow rate, which can easily be converted to a volumetric flow rate for use in Equation 4. Normal engineering principles should be used to ensure that the proper units (preferably SI units) are used in applying Equation 4.

In performing In-Plane Permeability measurements, it is important that the sample be uniformly compressed against the restraining surfaces to prevent large channels or openings that would provide paths of least resistance for substantial liquid flow that could bypass much of the sample itself. Ideally, the liquid will flow uniformly through the sample, and this can be ascertained by injecting dyed fluid into the sample and observing the shape of the dyed region through the transparent support plate. Injected dye should spread out uniformly from the injection point. In isotropic samples, the shape of the moving dye region should be nearly circular. In materials with in-plane anisotropy due to fiber orientation or small-scale structural orientation, the shape of the dye region should be oval or elliptical, and nearly symmetric about the injection point. A suitable dye for such tests is Versatint Purple II made by Milliken Chemical Corp. (Inman, S.C.). This is a fugitive dye that does not absorb onto cellulose, allowing for easy visualization of liquid flow through the fibrous medium.

In addition to specifying the average In-Plane Permeability, the ratio of the two in-plane components, or the in-plane anisotropy factor, $\alpha$, is also of interest. This factor is the ratio of the x-direction to y-direction permeability components, or $$\alpha = K_x/K_y \tag{5}$$

Radial flow tests performed with dyed fluid can be used to determine the in-plane anisotropy factor, using an approximate solution to the fluid flow equations obtained by J. D. Lindsay in "The Anisotropic Permeability of Paper: Theory, Measurements, and Analytical Tools," IPC Technical Paper Series No. 289, Institute of Paper Science and Technology, Atlanta, Ga., July 1988, and applied in J. D. Lindsay, "The Anisotropic Permeability of Paper," Tappi J., 73(5): 223 (May 1990). To relate in-plane anisotropy to the shape of a moving dye boundary resulting from injection of dye into a disk saturated with clear water, Lindsay obtained an approximate analytical solution in polar coordinates by neglecting flow in the tangential or q-direction. In the selected polar coordinate frame, q=0 corresponds to the x-direction and q=p/2 to the y-direction. Let $R_x$ and $R_y$ be the radial locations of the dye boundary in the x- and y-directions, respectively. Then the approximate solution allows $\alpha$ to be determined from the geometry of the colored zone from the equation:

$$\alpha = \frac{(R_x^2 - R_i^2)}{(R_y^2 - R_i^2)} \tag{6}$$

where Rhd iis the radius of the injection port at the center of the paper disk. This approximate solution was found to be highly accurate (when compared to numerical solutions of the flow problem) for the case of dye injected into a saturated disk and was also reasonably accurate for the case of dye injected into an initially dry disk.

For the In-Plane Permeability results to be a proper measure of the material in question, the permeability should reflect the resistance of the material itself and not the resistance of a large scale channel or void which has been created in some manner such as cutting, slitting, folding, pleating, etc. We therefore require that the material provide a radial flow uniformity that can be assessed by visualization of dye flow injected into the sample. Radial flow uniformity exists when dye injected into a dry sample with the previously described in-plane permeability apparatus results in a symmetric, roughly elliptical dye pattern. Such a dye pattern should yield a value of $\alpha$ (from Equation 6) less than 4 when $R_x$ is taken to be the radial position of the portion of the dye boundary furthest from the inlet, and $R_y$ is the radial position of the portion of the boundary closest to the inlet, at a time when $R_x$ is between 1 and 2 inches. If a sample with longitudinal channels is tested in this manner, there will be rapid flow in the longitudinal direction as fluid gushes through the channels, but in other flow directions (along paths proceeding radially outward from the periphery of the inlet port) that do not align well with the open channels, the flow will be much slower, resulting in a moving dye boundary that is greatly extended in the direction of the channels but which travels much less in other directions. Such a moving dye boundary will be irregular, possibly asymmetric, and will have long path lengths in some directions but much shorter path lengths in others, yielding $\alpha$ values over 4. Values of $\alpha$ as great as 2 may be achieved in machine made papers due to fiber orientation, so a limiting value of 4 has been selected to distinguish the effects of macroscopic nonuniformities from the effects of inherent small scale sheet structures on the measured In-Plane Permeability.

Three-dimensional materials for absorbent articles in which a structure is obtained by folding, pleating, cutting, etc., to generate a macroscopic structure lack the uniform nature of the material of the present invention. While the material of the present invention can be so arranged in various three-dimensional methods, it is important to differentiate the high In-Plane Permeability intrinsic to the materials of the present invention from the possibility of high In-Plane Permeability results obtained from macroscopic structures (those which do not have a representative unit area less than about 15 mm. by 15 mm. using the concept of representative elementary area in the sense known to those skilled in the art of flow through porous media and as explained by Jacob Bear in Chapter 1 of *Dynamics of Fluids in Porous Media,* Elsevier Publications Company, 1972, or those which do not have a nearly uniform basis weight distribution). For example, a pleated and folded structure may have long, macroscopic channels in the direction of folding which can provide large, open pathways for fluid flow. Such a material could be positioned in such a manner that it would offer little flow resistance in measurements of In-Plane Permeability, for the fluid would be flowing in the open channels, not through the sheet. High In-Plane Permeability results must be obtained in a structure with an a value less than 4 when measured with dilute aqueous, fugitive dye injection into the dry material, as described previously. An important advantage to having the sheet be uniform with respect to large length scales is that the uniform material provides continuous wicking paths and prevents fluid leakage through large channels. The surface pores and other three-dimensional structures are small enough to still provide capillary transport and good fluid retention, whereas pleated, folded, cut, or other large-scale three-dimensional sheets have channels which are ineffective at capillary transport because of their large diameter and which also can promote leaking.

The radial uniformity of flow in typical materials of the present invention is demonstrated in FIGS. 26 and 27, which are photographs of dye injection experiments, with optical access to the moving dye boundary made possible by a mirror at a 450 angle below the Plexiglas support plate of the permeability apparatus. The camera is directed towards the mirror which provides a view of the underside of the clear support plate, where the growth of the dye boundary is visible. In these tests, an aqueous dye solution was prepared from 40 ml of 7% Versatint Purple II dye (Milliken Chemical, Inman, S.C.) added to 1000 ml of deionized water. FIG. 26 shows successive images of the moving dye boundary advancing in a stack of two disks of dry material from the present invention, an uncreped through-air-dried 40 gsm basesheet of spruce BCTMP produced with 30 lbs. of Kymene per ton of fiber. The motion of the fluid is slightly faster in the machine direction, resulting in an elliptical shape aligned with the machine direction of the paper. Application of Equation 6 for FIGS. 26A and 26B results in α values of 1.70 and 1.76, respectively (edge effects in FIG. 26C have hindered flow in the machine direction, resulting in a lower α value of about 1.6). FIG. 27 shows a moving dye boundary in a slightly moistened 60 gsm basesheet of spruce BCTMP with 20 lbs. of Kymene added per ton of fiber, made with a T-116-1 throughdrying fabric (Lindsay Wire Division, Appleton Mills, Appleton, Wis.). An α value of about 1.4 is obtained in this case. These dye injection tests also show that the motion of the dye is through the porous medium and not through large channels in the sheet or through random gaps between the sample and the constraining surfaces.

As will be illustrated in the Examples, the webs of this invention possess very high In-Plane Permeability. More specifically, the In-Plane Permeability can be about $5 \times 10^{-11}$ square meters or greater, more specifically about $8 \times 10^{-11}$ square meters or greater, more specifically about $10 \times 10^{-11}$ square meters or greater, still more specifically from about $5 \times 10^{-11}$ to about $80 \times 10^{-11}$ square meters, and still more specifically from about $8 \times 10^{-11}$ to about $30 \times 10^{-11}$ square meters.

The "FIFE Test" is substantially as described in U.S. Pat. No. 5,147,343 issued Sep. 15, 1992 to Kellenberger entitled "Absorbent Products Containing Hydrogels With Ability To Swell Against Pressure", which is herein incorporated by reference. For purposes herein, the FIFE Test is carried out as described except for the following differences: the raised platform on the lower plate has been removed, so the lower surface is entirely flat; the sample area is 8 inches square and the blotter paper sheets are also cut to this size; multiple sheets were used to obtain a stack with a basis weight of about 240 gsm (roughly 10 grams total mass); samples were tested with a thin layer of poly film beneath them to enable them to be picked up more easily for flowback measurement; and each liquid insult was 40 milliliters. Since actual sample masses will vary slightly from the target of 10 grams, insult times are normalized to a mass of 10.0 grams by multiplying each observed intake time by a factor of (conditioned dry sample mass/10 grams). The combined time of the first, second and third insults is the FIFE Test value of the sample.

The webs of this invention can have FIFE Test values of about 125 seconds or less, more specifically about 75 seconds or less, still more specifically about 25 seconds or less, and still more specifically from about 25 to about 100 seconds.

The "Dry Wipe Residue" test provides a means of quantifying the ability of a web to wipe a surface dry. This property is of particular interest for products such as wipes, paper towels, cleaning articles and absorbent articles. To carry out this test, a piece of material approximating kitchen towel dimensions is attached to an 8 inches×8 inches×½ inch aluminum plate with adhesive tape. The material is wrapped over the top of the plate and taped there. There is a ½ inch diameter hole in the center of the plate. The plate with the material wrapped over it is illustrated in FIG. 17. It is placed on a 10 inches×12 inches×⅛ inch clear glass plate. A 3 cubic centimeter insult of 0.5% MBNS dye solution (Keystone Aniline, Chicago, Ill., available at 10.5% solids) is imparted into the hole and 10 seconds is allowed for absorption. The plate is then picked up vertically and the pattern on the glass allowed to dry (about 20 minutes). The glass plate is then placed dye-side down on a sheet of pink paper (Neenah Bond 02651, Neenah Paper Company, Neenah, Wis.) to provide optical contrast for imaging the blue dye against the paper when viewed through the opposite side of the glass plate. The residues are imaged with a Quantimet 900 Image Analysis system (Leica, Inc., Deerfield, Ill.) using the optical set-up and conditions shown by the following routine, "WIN1".

```
Cambridge Instruments QUANTIMET 900 QUIPS/MX   : V03.02 USER   : NEENAH
ANALYTICAL
ROUTINE   : WIN1      DATE   : 27-FEB-96      RUN   : 0 SPECIMEN   :
    COND = 35mm Nikkon Lens, f/4, 90 cm Pole-posn (autosts);"
        4 Incandescent Floods; Pink Paper W/ Residues down; .5% MBNS
        soln
Enter specimen identity
Scanner       ( No. 2 Newvicon LV= 0.00 SENS= 1.65 PAUSE
Load Shading Corrector   ( pattern - SCLIN1)
Calibrate User Specified   (Calibration Value = 0.2170 millimetres per
pixel)
CALL STANDARD
TOTPERCAR   := 0.
TOTFIELDS   := 0.
TOTSIZE     := 0.
TOTSPACIN   := 0.
TOTSHAPE    := 0.
TOTAREA     := 0.
TOTAVEBRT   := 0.
TOTDARK     := 0.
TOTMASS     := 0.
For FIELD
Detect 2D  ( Darker than 57 PAUSE )     [Comment: adjust as needed]
Amend      ( OPEN by 0 )
Pause Message
EDIT OUT ANY ARTIFACTS . . . .
Edit (pause)
Measure field - Parameters into array FIELD
Measure field - Integrated Brightness masked by Binary into array FIELD
AREA          := FIELD AREA
AVEBRIGHT     := ( FIELD TOTBRIGHT / ( AREA / ( CAL.CONST CAL.CONST ) ) )
SIZE          := FIELD AREA / ( ( FIELD V.PROJECT + FIELD H.PROJECT ) / 2.
)
ANISOT        := 1. / FIELD ANISOTRPY
TEMP          := ( FIELD V. PROJECT + FILED H. PROJECT ) / 2.
DARKNESS      := 64. - AVEBRIGHT
MASSFACT      := AREA * DARKNESS / 1000.
Detect 2D       ( Darker than 9 )
Pause Message
DRAW PATTERN CIRCLE AROUND DOTS . . .
Edit (pause)
Measure field - Parameters into array FIELD
PATTERN      := FIELD AREA
PERCAREA     := 100. * AREA / PATTERN
SPACING      := ( PATTERN - AREA ) / TEMP
TOTAREA      := TOTAREA + AREA
TOTPERCAR    := TOTPERCAR + PERCAREA
TOTSIZE      := TOTSIZE + SIZE
TOTSPACIN    := TOTSPACIN + SPACINC
TOTSHAPE     := TOTSHAPE + ANISOT
TOTAVEBRT    := TOTAVEBRT + AVEBRIGHT
TOTDARK      := TOTDARK + DARKNESS
TOTMASS      := TOTMASS + MASSFACT
TOTFIELDS    := TOTFIELDS + 1.
Pause Message
PLEASE CHOOSE ANOTHER FIELD, OR 'FINISH'. . .
Pause
Next FIELD
Print       " "
Print      "AVE TOTAL AREA ( sq mm) = ", TOTAREA / TOTFIELDS
Print       " "
Print      "PERCENT COVERAGE = ", TOTPERCAR / TOTFIELDS
Print       " "
Print      "AVERAGE SIZE (mm) = ", TOTSIZE / TOTFIELDS
Print       " "
Print      "AVERAGE SPACING (mm) = ", TOTSPACIN / TOTFIELDS
Print       " "
Print      "AVEPAGE SHAPE = ", TOTSHAPE / TOTFIELDS
Print       " "
Print      "AVE DARKNESS (masked) - ", TOTDARK / TOTFIELDS
Print       " "
Print      "AVE MASS FACTOR = ", TOTMASS / TOTFIELDS
Print       " "
Print      "TOTAL NUMBER OF FIELDS = ", TOTFIELDS
For LOOPCOUNT = 1 to 5
Print       " "
Next
End of Program
```

The results of the Dry Wipe Residue testing provide a Total Area coverage for the residue, a percent area coverage of the residue and a Mass Factor (area * darkness/1000) which represents the mass of material in the residue. The "Total Area" of the residues pattern is simply the sum of all "black" pixels in the image of the residues pattern, regardless of how deeply black they might be. In practice, the detection level is set to accept all pixels from 0 to about 55 (adjust as needed) on a 6-bit gray scale running from 0 to 64. The "Mass Factor" is a parameter that weights the area of the image of the residues by the mean gray level underlying all pixels and dividing by 1000 to generate more manageable numbers. This has been shown to give a value approximately proportionate to the mass (milligrams) remaining on the glass plate, provided that optical saturation does not occur (i.e., there are not very dark residues regions present). The "percent coverage" is simply 100 times the ratio of the area of the "black" pixels within the boundary of the image "Total Area" to the entire area enclosed in a cover region drawn around the residues pattern using the mouse editor.

Webs of this invention can have Dry Wipe Residue Total Area coverage values of about 2000 square mm. or less, more specifically about 1500 square mm. or less, and still more specifically from about 500 to about 1000 square mm. The Dry Wipe Residue Mass Factor can be about 30 or less, more specifically about 20 or less, and still more specifically from about 5 to about 20 or 30.

A test similar to the Dry Wipe Residue test just described is the "Wet Wipe Residue" test, which is conducted with an initially saturated wet sheet rather than starting with a dry sheet. Specifically, a 3 inches×3 inches piece of the test material is truncated at ⅓ edge distances to form an octagon as illustrated in FIG. 18. The octagonal test material is placed in a 100 millimeter crystallization dish and saturated to 350 weight percent with a 0.5% MBNS solution as described above. The area of the octagon is about 7 square inches. The dwell time for saturation is 3 minutes. The saturated material is picked up with a tweezers and placed on a 10 inches×12 inches×⅛ inch clear glass plate. An 8 inches×8 inches×1 inch piece of aluminum is placed on top of the material and allowed to dwell for 30 seconds. The plate is then picked up vertically and the test material removed from the glass plate with tweezers. The residues are allowed to dry (about 5 minutes). (See FIG. 19.) The plate is placed dye-side down on a sheet of pink paper as described above and the residues are imaged with a Quantimet 900 Image Analysis system using the same optical set-up and imaging conditions shown by the "WIN1" routine identified above.

As with the Dry Wipe Residues test, the same "WIN1" routine yields values for Total Area and percent area coverage by the residues and a Mass Factor for the residues. Webs of this invention can have a Wet Wipe Residue Total Area coverage of about 1500 square mm. or less, more specifically about 1000 square mm. or less, and still more specifically from about 400 to about 800 square mm. The Mass Factor for the Wet Wipe Residue test can be about or less, more specifically from about 2 to about 5.

Some of the webs of this invention may also be characterized in part by the "Mean Volume-Weighted Pore Length", expressed in microns. This structural parameter is related to the wicking ability of the material when wetted. The Mean Volume-Weighted Pore Length is determined by placing a 6 inches×6 inches piece of the material to be tested on a plastic sheet (e.g. "Glad Wrap" or similar material) on a horizontal flat surface. The sample is then flooded with distilled water. The material is allowed to dry over night at less than 40% relative humidity. Subsections of the dried material are cut off and cross-sectioned under liquid nitrogen for back-scattered electron photomicroscopy as described in U.S. Pat. No. 5,492,598 issued Feb. 20, 1996 to Hermans et al. entitled "Method for Increasing the Internal Bulk of Throughdried Tissue", which is herein incorporated by reference. However, for purposes of measuring Mean Volume-Weighted Pore Length, only 7 photos are taken at a constant 50×magnification for all samples. The photos are not assembled into a photomontage, but placed individually under plate glass on a Kreonite Macroviewer (J. Kelly, Inc., Darien, Ill.) and viewed with a 50 mm. EL-Nikkor lens (Nikon, Inc., OEM Sales Group, Melville, N.Y.). The image is oriented horizontally across the photo as illustrated in FIG. 23 and analyzed by the routine "TSAI3" which follows below. The cross-section boundaries are selected by ACCEPT and REJECT operations using "mouse" EDIT on the Quantimet 970 Image Analysis System (Leica, Inc., Deerfield, Ill.). The parameters are described by equations in "TSAI3".

---

```
Cambridge Instruments QUANTIMET 970    QUIPs/MX: V08.00    USER : NEENAH
ANALYTICAL
ROUTINE : TSAI3    DATE : 26-FEB-96    RUN: 1 SPECIMEN : #4CHF   40GSM 20PPT K
        COND = 50mm EL-Nikkor Lens: 2 1/4" field of view, 4 photofloods on
             Kreonite Macroviewer; Horizontal section orientation
Scanner        ( No. 1 Chalnicon LV   0.00 SENS= 1.94 PAUSE )
SUPRTN STANDARD
Load Shading Corrector   ( pattern - LINERO)
Calibrate User Specified (Cal Value = 1.393 microns per pixel)
FLAG3          :=     3.
Pause Message
       Please Position Sample
Pause
TOTFIELDS          :=     0.
Enter specimen identity
For FIELD
Scanner         ( No. 1 Chalnicon LV= 0.00 SENS= 1.94 PAUSE )
Live Frame is Standard Image Frame
Image Frame is Rectangle ( X: 12, Y: 15, W: 860, H: 668, )
Detect 2D     ( Darker than 32, Delin PAUSE )
Amend ( OPEN by 1 )
Edit (pause) EDIT          [Comment:for "ACCEPT" of cross-section only,
                            and "REJECT" of background region.]
```

-continued

```
TOTFIELDS         :=TOTFIELDS + 1.
Measure feature     AREA    PERIMETER    LENGTH
    using 32 ferets
    into array FEATURE1 ( of 500 features and 7 parameters )
FEATURE1 CALC.A    :=( (PERIMETER/2. ) - (2.*AREA/PERIMETER)) [Comment:pore length]
FEATURE1 CALC.B    := 0.84880 * AREA * AREA / LENGTH [Comment:pore volume]
Distribution of COUNT v CALC.A (Units MICRONS )
    from FEATURE1 in HIST02 from 1.000 to 2000.
    in 10 bins (LOG)
Distribution of CALC.B (Units CUMICRONS ) v CALC.A ( Units MICRONS )
    from FEATURE1 in HIST03 from 1.000 to 2000.
    in 10 bins (LOG)
Pause
Next FIELD
Print      " "
Print      " "
Print      Distribution ( HIST02, + cummlative, bar chart, scale =     0.00 )
Print      "COUNT VS TRUE LENGTH,  um"
Print      " "
Print      " "
Print      Distribution ( HIST03, + cumulative, bar chart, scale =     0.00 )
                                [Comment:The volume-weighted mean Print "CUM
                                ELLIP VOL % VS TRUE LENGTH, um" pore length
                                (um) is read from this histogram.]
Print      " "
Print      "TOTAL NUMBER OF FIELDS ( PHOTOS) = ", TOTFIELDS
For LOOPCOUNT =     1 to 13
Print      " "
Next
End of PROGRAM
```

Some of the webs of this invention can have a Mean Volume-Weighted Pore Length of about 550 microns or greater, more specifically about 700 microns or greater, and still more specifically from about 600 to about 1000 microns.

Additionally, the webs of this invention have a substantially uniform thickness, as evidenced by a relatively low thickness percent coefficient of variation (%COV), referred to herein as the Thickness Variation Index. The Thickness Variation Index can be about 25 percent or less, more specifically from about 5 to about 15 percent. To determine the thickness percent coefficient of variation, photomicrograph montages of tissue cross-sections are prepared by the scanning electron-microscopy method described in U.S. Pat. No. 5,492,598 incorporated by reference above (on tissues that were not previously wetted). For this method, however, montages need not be assembled (since autostage control is unnecessary) and the ideal magnification of 50× can be held constant across all photos. Individual photos were viewed in horizontal orientation (FIG. 28A) with a 50 mm. EL-Nikkor lens that provides a 2¼ inches field of view with the Chalnicon scanner attached to a Quantimet 970 Image Analysis System. Illumination is provided by a Kreonite Macroviewer using 4 photo-flood lamps. Using the routine "TSAI2" set forth below, the image of the tissue cross-section is filled as a solid detection region (FIG. 28B) by various binary operations and then "LINE" slices are taken at local maxima and minima to represent thickness samples (FIG. 28C). These are assembled into a histogram from which MEAN and standard deviation values are extracted for $\%COV=100(\sigma/\mu)$.

```
Cambridge Instruments  QUANTIMET 970   QUIPS/MX:   V08.00   USER : NEENAH ANALYTICAL
ROUTINE : TSAI2    DATE : 28-FEB-96    RUN : 3 SPECIMEN : #4 CHF 40GSM 20PPT K
AUTH = B. E. KRESSNER
DATE = 24 APR 1995
COND = ANY INPUT, PHOTO OR LIVE FOAM IMAGE.
Scanner     ( No. 1 Chalnicon LV= 0.00 SENS= 1.94 PAUSE )
SUBRTN STANDARD
Load Shading Corrector    ( pattern - LINERO)
Calibrate User Specified (Cal Value = 0.6964 microns   per pixel)
                                [Comment: change as appropriate for
                                photo magnification]
FLAG3 := 3.
Pause Message
    Please Position Sample
Pause
TOTCLOSAP    := 0.
TOTFIELDS    := 0.
Enter specimen identity
For FIELD
Scanner     ( No. 1 Chalnicon LV=0.00 SENS= 1.94 PAUSE )
Live Frame is Standard Image Frame
Image Frame is Rectangle ( X: 12, Y: 15, W: 860, H:668, )
```

-continued

```
Detect 2D   ( Lighter than 32, Delin PAUSE )
Amend    ( OPEN by 1 )
Edit (pause) DRAW          [Comment:for the "planting of a dilation
                            seed at edges of photo to insure true
                            section thickness]
Amend    ( CLOSE by 25 )
Image Transfer from Binary B <FILL HOLES> to Binary Output
Amend    ( OPEN by 25 )
Edit    (pause) EDIT       [Comment:to take vertical "LINE" slices at
                            local maxima and minima down the section
                            length.]
Measure feature    AREA     PERIMETER    LENGTH
    using 32 ferets
    into array FEATURE1 ( of 500 features and 7 parameters )
Accept FEATURE1 LENGTH from      0. to 487.    [Comment:change as needed]
Distribution of COUNT v LENGTH    (Units MICRONS )
    from FEATURE1 in HIST01 from 100.0 to 500.0    [Comment:change as needed]
    in bins (LIN)
Distribution of COUNT v LENGTH    (Units MICRONS )
    from FEATURE1 in HIST03 from 50.00 to 950.0
    in 20 bins (LIN)
Pause
Next FIELD
Print      " "
Print    Distribution HIST01, differential, bar chart, scale = 0.00 )
                            [Comment:The mean and standard deviation
                            from this histogram are used to
                            calculate % COV, =100*(δ/μ)]
Print      " "
Print      " "
Print    Distribution ( HIST03, differential, bar chart, scale = 0.00 )
Print      " "
Print      " "
END OF PROGRAM
```

BRIEF DESCRIPTION OF THE DRAWINGS

FIG. 4A illustrates the Overall Surface Depth profile to Sample U2. FIG. 4B illustrates the fine structure surface depth (P10) for a 35 mm. long profile taken along an elevated region of Sample U2. FIG. 4C illustrates the surface depth of Sample U2 taken along a line dominated by low knuckle areas.

FIG. 5 illustrates the Overall Surface Depth profile of Sample U8 (P10=0.509 mm).

FIG. 10 is a table identifying Samples U1–U10.

FIG. 11 is a table summarizing the results of the wet resiliency testing.

FIG. 13 is a table summarizing wet resiliency testing for air-laid materials.

FIG. 14 is a table summarizing the In-Plane Permeability test results for various materials.

FIG. 15 is a table summarizing the FIFE test results for various samples, expressed in seconds. The times have been normalized to 10 grams of sample weight (original FIFE time×dry weight/10 grams).

FIG. 20 is a table summarizing the results of the Dry Wipe Residue tests.

FIG. 21 is a table summarizing the results of the Wet Wipe Residue tests.

FIGS. 28A, 28B and 28C are illustrations of photographs used to determine the Thickness Variation Index.

DETAILED DESCRIPTION OF THE DRAWING

Figure 1:
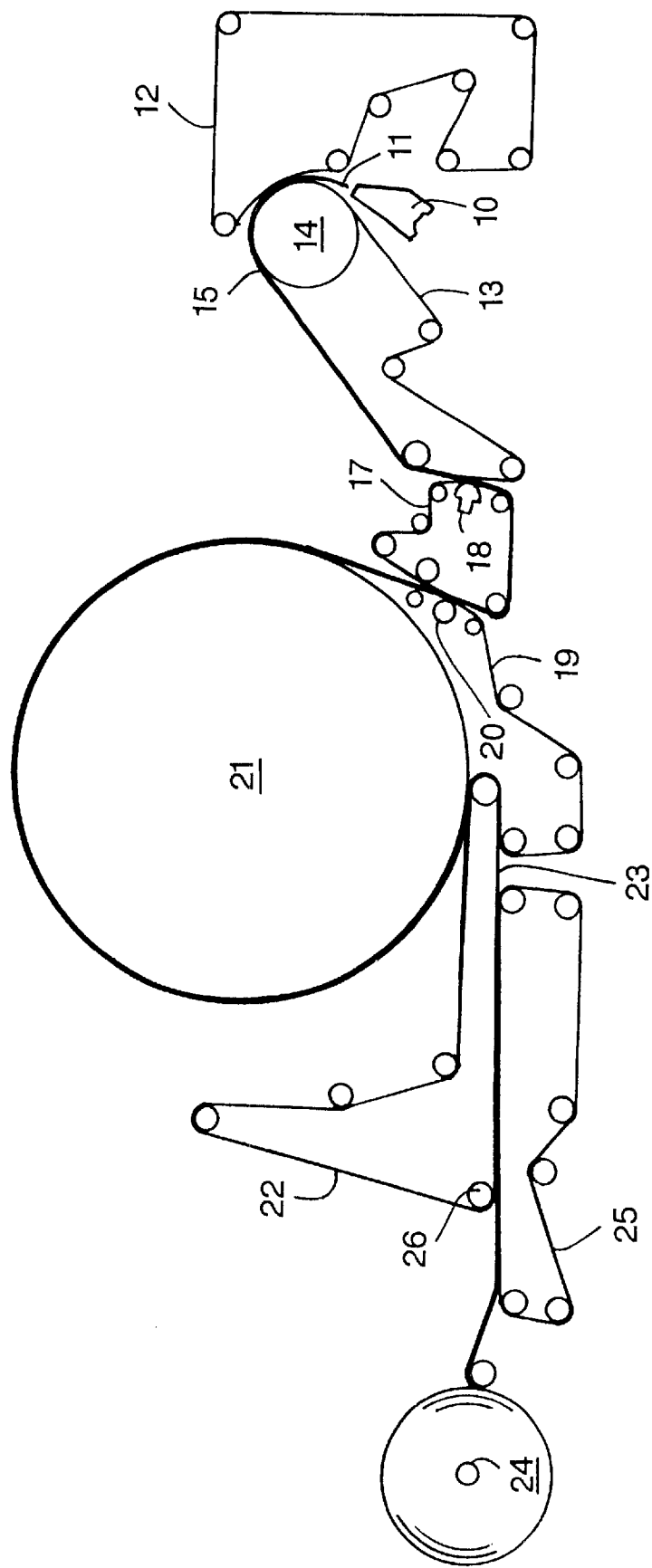
FIG. 1 is a schematic diagram of an uncreped through-dried papermaking process useful for making wet resilient absorbent structures of this invention.
Figure 2:
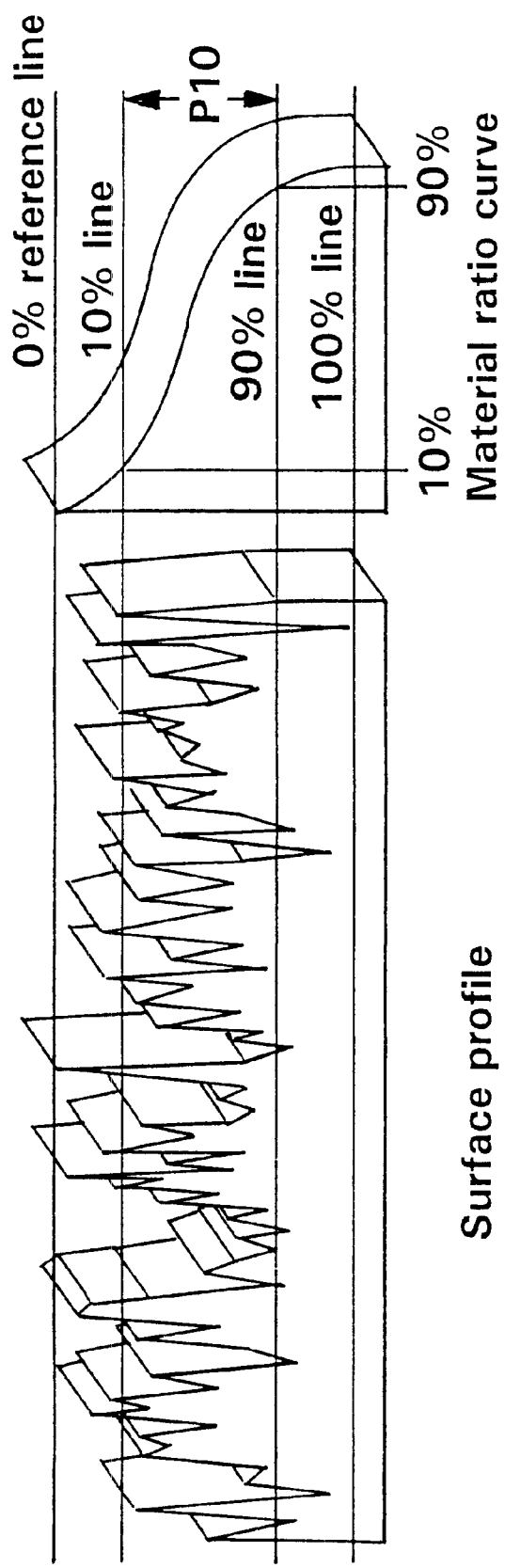
FIG. 2 is a surface profile illustrating the relationship between a surface profile and its material ratio curve. Also shown are the 10% and 90% material lines used to define the "P10" peak height parameter.
Figure 3A:
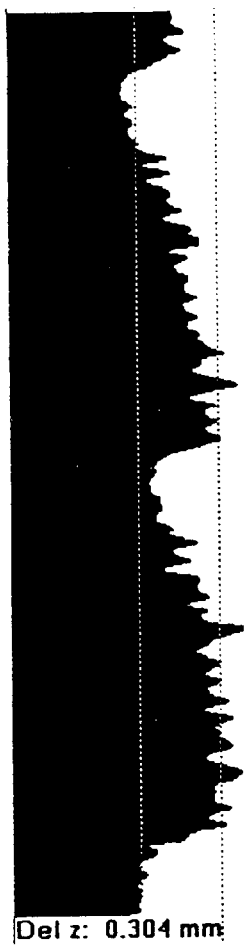
FIG. 3A illustrates the Overall Surface Depth profile of a Surpass hand towel.
Figure 3B:
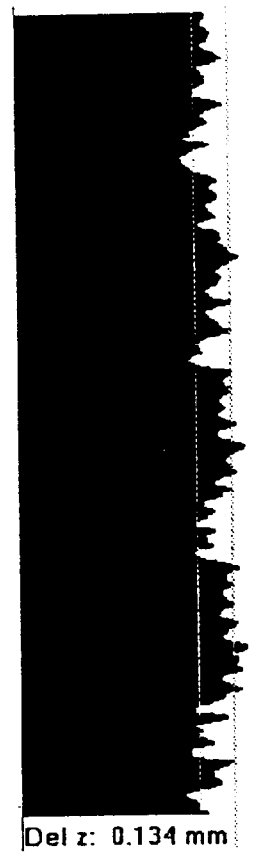
FIG. 3B is the fine structure surface depth profile of the same sample.
Figure 3C:
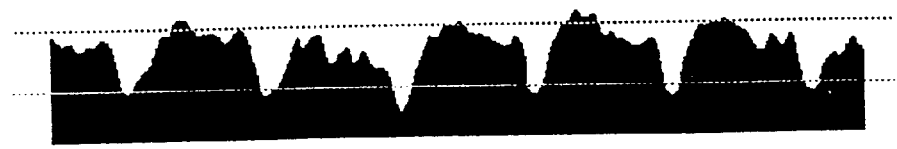
FIG. 3C is the overall Surface Depth profile in the cross-machine direction.
Figure 6:
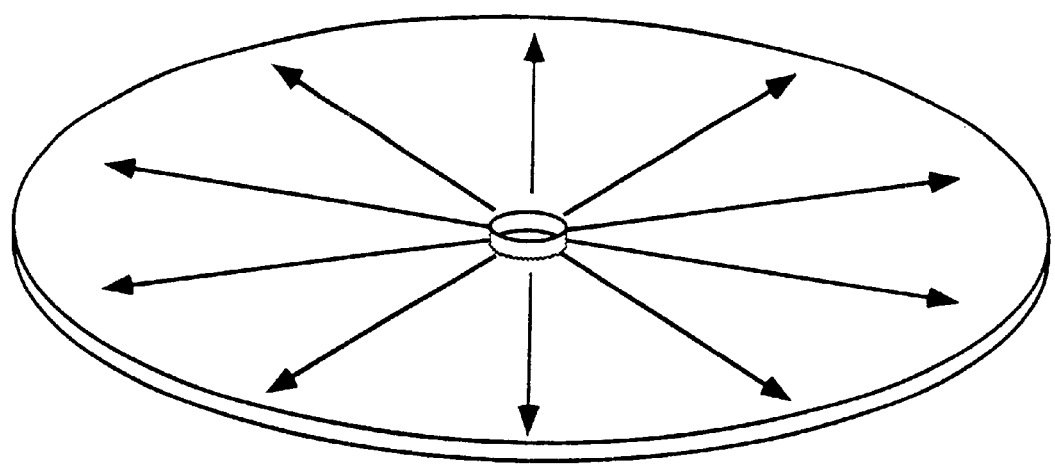
FIG. 6 illustrates the flow pattern in a paper disk during In-Plane Permeability measurement (angle view).
Figure 7:
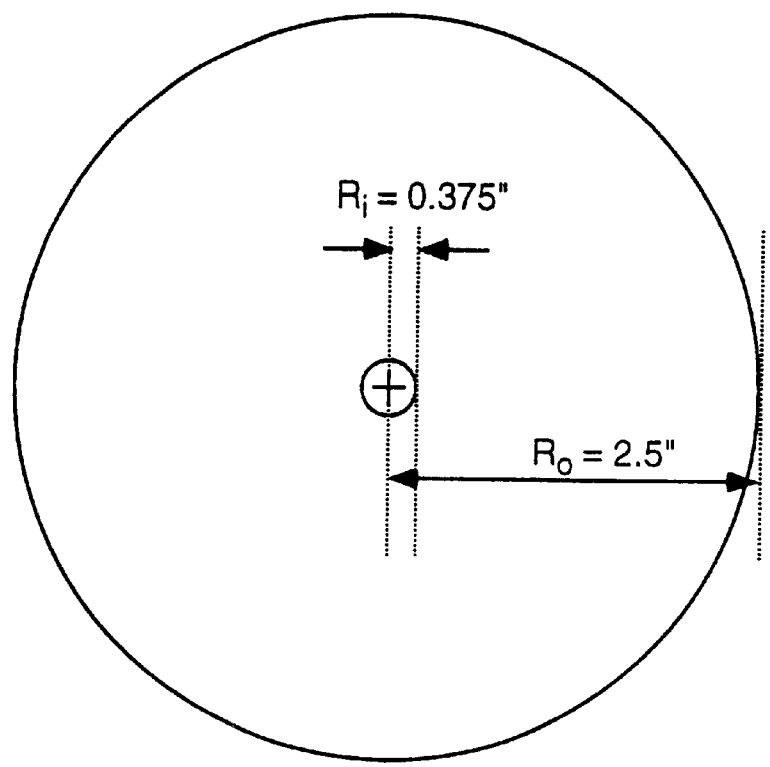
FIG. 7 is a plan view of the paper disk used for In-Plane Permeability testing, illustrating the dimensions of the disk.
Figure 8:
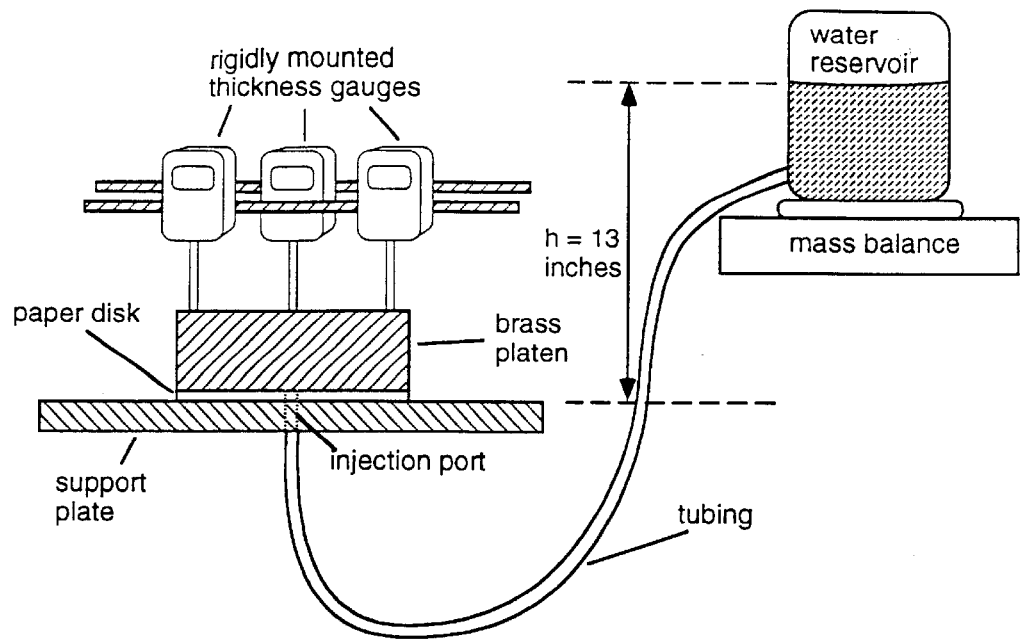
FIG. 8 is a schematic side view of the apparatus used for In-Plane Permeability testing.
Figure 9:
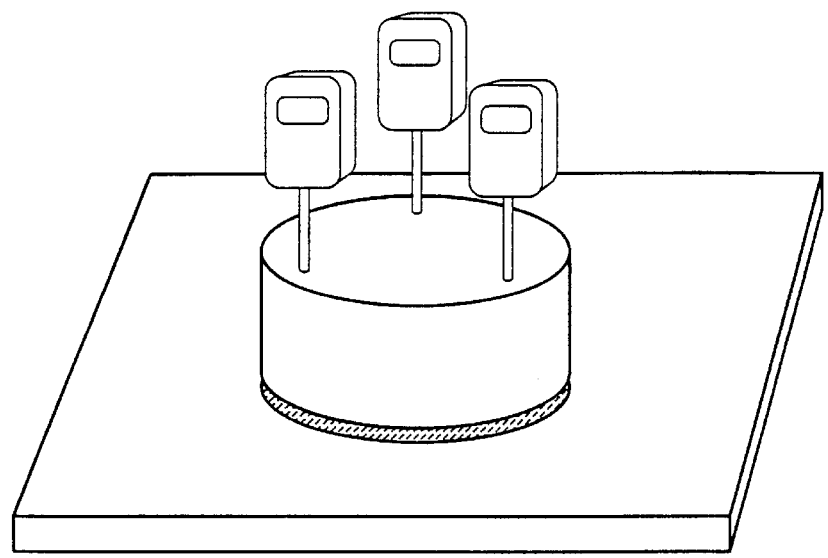
FIG. 9 is a perspective view of the brass platen and thickness gauges used for In-Plane Permeability testing.

Referring to FIG. 1, shown is a method for making throughdried paper sheets in accordance with this invention. (For simplicity, the various tensioning rolls schematically used to define the several fabric runs are shown but not numbered. It will be appreciated that variations from the apparatus and method illustrated in FIG. 1 can be made without departing from the scope of the invention). Shown is a twin wire former having a layered papermaking headbox 10 which injects or deposits a stream 11 of an aqueous suspension of papermaking fibers onto the forming fabric 13 which serves to support and carry the newly-formed wet web downstream in the process as the web is partially dewatered to a consistency of about 10 dry weight percent. Additional dewatering of the wet web can be carried out, such as by vacuum suction, while the wet web is supported by the forming fabric.

The wet web is then transferred from the forming fabric to a transfer fabric 17 traveling at a slower speed than the forming fabric in order to impart increased stretch into the web. This is commonly referred to as a "rush" transfer. Preferably the transfer fabric can have a void volume that is equal to or less than that of the forming fabric. The relative speed difference between the two fabrics can be from 0–60 percent, more specifically from about 10–40 percent. Transfer is preferably carried out with the assistance of a vacuum shoe 18 such that the forming fabric and the transfer fabric simultaneously converge and diverge at the leading edge of the vacuum slot.

The web is then transferred from the transfer fabric to the throughdrying fabric 19 with the aid of a vacuum transfer roll 20 or a vacuum transfer shoe, optionally again using a fixed gap transfer as previously described. The throughdrying fabric can be traveling at about the same speed or a different speed relative to the transfer fabric. If desired, the throughdrying fabric can be run at a slower speed to further enhance stretch. Transfer is preferably carried out with vacuum assistance to ensure deformation of the sheet to conform to the throughdrying fabric, thus yielding desired bulk and appearance. Suitable throughdrying fabrics are described in U.S. Pat. No. 5,429,686 issued to Kai F. Chiu et al., previously incorporated by reference.

The level of vacuum used for the web transfers can be from about 3 to about 15 inches of mercury (75 to about 380 millimeters of mercury), preferably about 5 inches (125 millimeters) of mercury. The vacuum shoe (negative pressure) can be supplemented or replaced by the use of positive pressure from the opposite side of the web to blow the web onto the next fabric in addition to or as a replacement for sucking it onto the next fabric with vacuum. Also, a vacuum roll or rolls can be used to replace the vacuum shoe(s).

While supported by the throughdrying fabric, the web is final dried to a consistency of about 94 percent or greater by the throughdryer 21 and thereafter transferred to a carrier fabric 22. The dried basesheet 23 is transported to the reel 24 using carrier fabric 22 and an optional carrier fabric 25. An optional pressurized turning roll 26 can be used to facilitate transfer of the web from carrier fabric 22 to fabric 25. Suitable carrier fabrics for this purpose are Albany International 84M or 94M and Asten 959 or 937, all of which are relatively smooth fabrics having a fine pattern. Although not shown, reel calendering or subsequent off-line calendering can be used to improve the smoothness and softness of the basesheet.

FIGS. 2–7 have already been discussed above.

FIGS. 8–23 will be described in connection with the Examples to follow.

Figure 24:
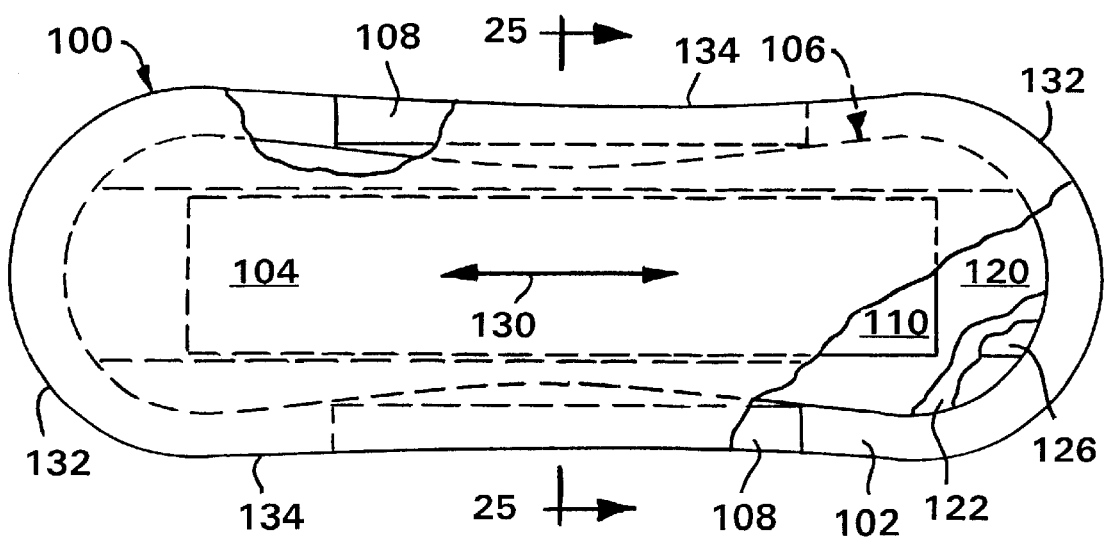
FIG. 24 is a top plan view of disposable absorbent article according to the present invention, taken from the inner bodyside of the absorbent article in a stretched and laid flat condition and with portions broken away for purposes of illustration.
Figure 25:
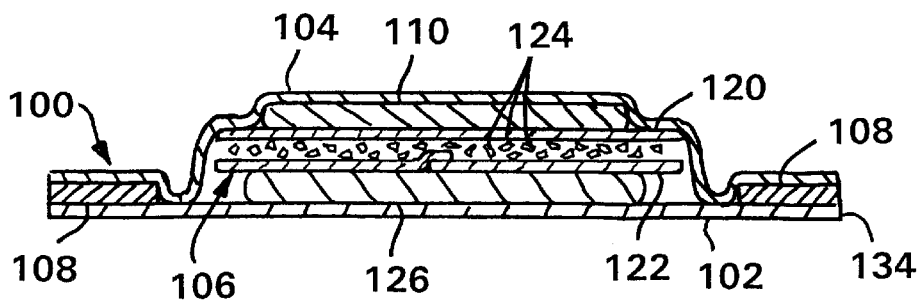
FIG. 25 is an enlarged transverse section view taken generally from the plane of the line 25—25 in FIG. 24.

FIGS. 24 and 25 show an absorbent article utilizing a web according to the present invention as illustrated by an incontinence pad 100. The pad 100 includes a moisture barrier 102, a bodyside liner 104, and a retention portion in the form of an absorbent assembly 106 disposed between the moisture barrier and bodyside liner. Desirably although not necessarily, the pad 100 may also include side elastic members 108 and a liquid acquisition/distribution layer 110. The pad 100 desirably further comprises a means for holding the pad 100 in position during use (not shown). For example, the pad 100 may comprise a garment attachment adhesive, a body attachment adhesive, belts, straps, wings, mechanical fasteners, and/or other suitable fastening devices to secure the pad in position to absorb body exudates.

The absorbent assembly 106 of the pad 100 comprises a thin, layered structure capable of providing a relatively large liquid retention capacity. The absorbent assembly 106 includes upper and lower sheets 120 and 122 according to the present invention with high-absorbency materials 124 disposed between the sheets. The liquid wicking properties of the sheets 120 and 122 enable particularly effective and efficient utilization of the high-absorbency materials 124. The absorbent assembly 106 desirably but not necessarily also includes a support layer 126 disposed between the sheets 120 and 122 and the moisture barrier 102. Other materials know in the art, such as odor adsorbing particles (not shown), may also be incorporated into the pad 100, and in particular into the absorbent assembly 106.

With particular reference to FIG. 24, the illustrated pad 100 defines a longitudinal axis or center line represented by arrow 130, which generally corresponds to the greatest planar dimension of the product. The pad 100 has opposite, longitudinal end edges 132 and opposite, longitudinal side edges 134 that extend between the longitudinal end edges. The longitudinal side edges 134 are shown as generally straight, but optionally, may be curvilinear and contoured, for example so that the pad 100 is generally hourglass shaped.

The moisture barrier 102 and bodyside liner 104 are desirably longer and wider than the absorbent assembly 106 so that the peripheries of the moisture barrier and bodyside liner may be bonded together using ultrasonic bonds, thermal bonds, adhesives, or other suitable means. Additionally, the absorbent assembly 106 may be bonded directly to the moisture barrier 102 and/or the bodyside liner 104 using ultrasonic bonds, thermal bonds, adhesives, or other suitable means. As used herein, the term bonded refers to the joining, adhering, connecting, attaching, or the like, of two elements. Two elements will be considered to be bonded together when they are bonded directly to one another or indirectly to one another, such as when each is directly bonded to intermediate elements.

The moisture barrier or backsheet 102 desirably comprises a material that is formed or treated to be liquid impermeable. Alternatively, the moisture barrier 102 may comprise a liquid permeable material and other suitable means may be provided to impede liquid movement away from the absorbent assembly 106, such as a liquid impermeable layer (not shown) associated with the absorbent assembly. The moisture barrier 102 may also be gas permeable over either all or part of its surface area.

The moisture barrier 102 may comprise a single layer of material or a laminate of two or more separate layers of material. Suitable moisture barrier materials include films, wovens, nonwovens, laminates of films, wovens, and/or nonwovens, or the like. For example, the moisture barrier 102 may comprise a thin, substantially liquid impermeable web or sheet of plastic film such as polyethylene, polypropylene, polyvinyl chloride or similar material. The moisture barrier material may be transparent or opaque and have an embossed or matte surface. One particular material for the moisture barrier 102 is a polyethylene film that has a nominal thickness of about 0.028 millimeter and a systematic matte embossed pattern, and that has been corona treated on both sides.

The absorbent assembly 106 comprises materials adapted to absorb, distribute, and retain liquid waste. The individual sheets 120 and 122 may be formed from a single web that is C-folded to enclose the high-absorbency materials 124 within an envelope. The sheets 120 and 122 and the high-absorbency materials 124 are desirably bonded together at least in a dry state by adhesives, chemical bonds, or other suitable means. The C-folded composite may then be cut or trimmed as needed, for example to provide the hourglass shaped structure as illustrated in FIGS. 24 and 25. Alternatively, the sheets 120 and 122 may comprise separate layers that are united during assembly of the pad 100.

The absorbent assembly 106 may include 0–95 weight percent of organic or inorganic high-absorbency materials to increase the absorbency of the assembly. As used herein, the term high-absorbency materials refers to materials that are capable of absorbing at least about 15 and desirably more than 25 times their weight in water. Suitable high-absorbency materials are described in U.S. Pat. No. 4,699,823 issued Oct. 13, 1987, to Kellenberger et al. and U.S. Pat. No. 5,147,343 issued Sep. 15,1992, to Kellenberger, which are incorporated herein by reference. High-absorbency materials are available from various commercial vendors, such as The Dow Chemical Company; Hoechst Celanese Corporation; Chemische Fabrik Stockhausen, GMBH; and Allied Colloids, Inc.

The support layer 126 desirably comprises materials that are adapted to absorb, distribute and retain liquid waste, and the support layer functions in part to enhance the ability of the pad 100 to resist twisting and roping during use. The support layer 126 may comprise various absorbent materials, such as an air-formed batt of cellulosic fibers (i.e., wood pulp fluff), a coform material composed of a mixture of cellulosic fibers and synthetic polymer fibers, and/or high-absorbency materials. By way of illustration, the support layer 126 may comprise a single, compressed layer of wood pulp fluff having a density of about 0.2 g/cc.

The acquisition/distribution layer 110 is desirably provided to help decelerate and diffuse surges of liquid that may be introduced into the absorbent assembly 106. The acquisition/distribution layer 110 may be positioned subjacent the bodyside liner 104 as illustrated, or alternatively disposed on the inwardly facing, bodyside surface of bodyside liner. Suitable configurations of the acquisition/distribution layer 110 are described in U.S. Pat. No. 5,192,606 issued Mar. 9, 1993, to D. Proxmire et al.; U.S. Pat. No. 5,486,166 issued Jan. 23, 1996 to Ellis et al.; U.S. Pat. No. 5,490,846 issued Feb. 13, 1996 to Ellis et al.; and U.S. patent application Ser. No. 096,654 of W. Hanson et al., titled "Thin Absorbent Article Having Rapid Uptake Of Liquid," and filed Jul. 22, 1993; the disclosures of which are hereby incorporated by reference. By way of illustration, the acquisition/distribution layer 110 may comprise a through-air bonded carded web composed of a blend of 40% of 6 denier polyester fibers, commercially available from Hoechst Celanese Corporation, and 60% of 3 denier polypropylene/polyethylene side-by-side bicomponent fibers, commercially available from BASF Corporation, and have an overall basis weight of from about 50 to about 120 gsm.

The bodyside liner or topsheet 104 is formed of a liquid permeable material so that liquid waste, and possibly semi-solid waste as well, can pass through the liner and be absorbed by the absorbent assembly 106. Suitable bodyside liners 104 may comprise a nonwoven web or sheet of wet strength tissue paper, an apertured film, a spunbonded, meltblown or bonded-carded web composed of synthetic polymer filaments or fibers, such as polypropylene, polyethylene, polyesters or the like, or a web of natural polymer filaments or fibers such as rayon or cotton. In addition, the bodyside liner 104 may be treated with a surfactant to aid in liquid transfer. In one particular embodiment, the liner 104 comprises a nonwoven, spunbond polypropylene fabric having a basis weight of about 17 gsm. The fabric is pin apertured and surface treated with a surfactant commercially available from Union Carbide Chemicals and Plastics Company, Inc. under the trade designation TRITON X-102. As used herein, the term fabric is used to refer to all of the woven, knitted and nonwoven fibrous webs. The term nonwoven web means a web of material that is formed without the aid of a textile weaving or knitting process.

In the illustrated embodiment, the elongated side elastic members 108 are longitudinally orientated contiguous with each side edge 134 and extend toward the end edges 132. The side elastic members 108 may be bonded in a stretched condition intermediate the moisture barrier 102 and the bodyside liner 104 using ultrasonic bonds, adhesives, thermal bonds, or other suitable means, in either a straight or a curved shape. Alternatively, the side elastic members 108 may be bonded in a relaxed state to a gathered portion of the moisture barrier 102, the bodyside liner 104, or both. As used herein, the terms elastic, elasticized and elasticity mean that property of a material by virtue of which it tends to recover its original size and shape after removal of a force causing a deformation.

The side elastic members 108 may be formed of a dry-spun coalesced multifilament elastomeric thread sold under the tradename LYCRA and available from E.I. Du Pont de Nemours and Company. Alternately, the elastic members may be formed of other typical elastics utilized in making incontinence products, such as a thin ribbon of natural rubber, a stretch bonded laminate material comprising a prestretched elastic meltblown inner layer sandwiched between and bonded to a pair of spunbond polypropylene nonwoven webs, or the like. Elasticity could also be imparted to the absorbent article by extruding a hot melt elastomeric adhesive between the moisture barrier 102 and the liner 104. Other suitable elastic gathering means are disclosed in U.S. Pat. No. 4,938,754 to Mesek and U.S. Pat. No. 4,388,075 to Mesek et al.

Figure 26A:
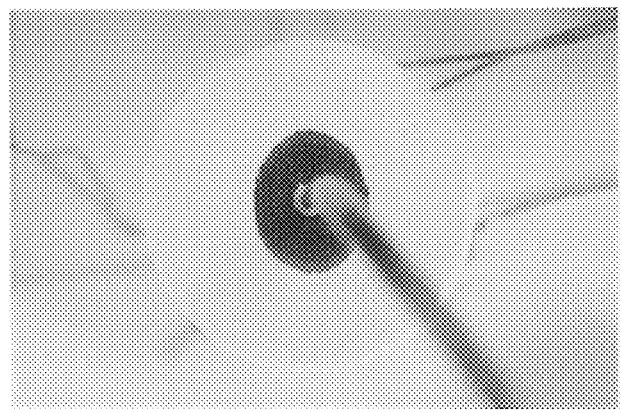
FIGS. 26a, b, and c are sequential photographs of dye injection into a dry, uncreped through-air-dried web of this invention, illustrating the permeability flow pattern.
Figure 26B:
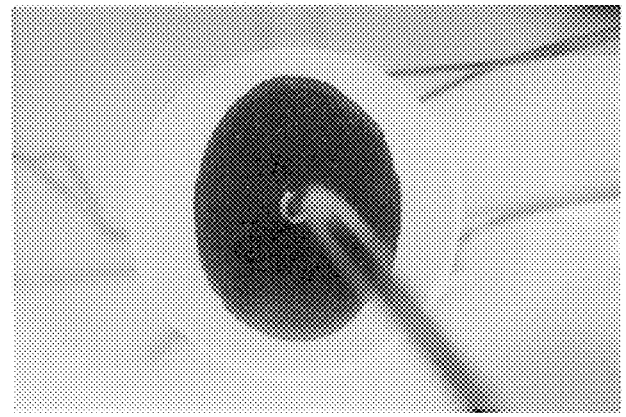
Figure 26C:
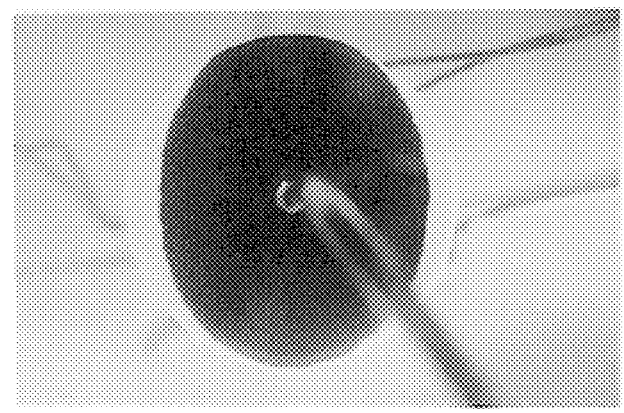
Figure 27:
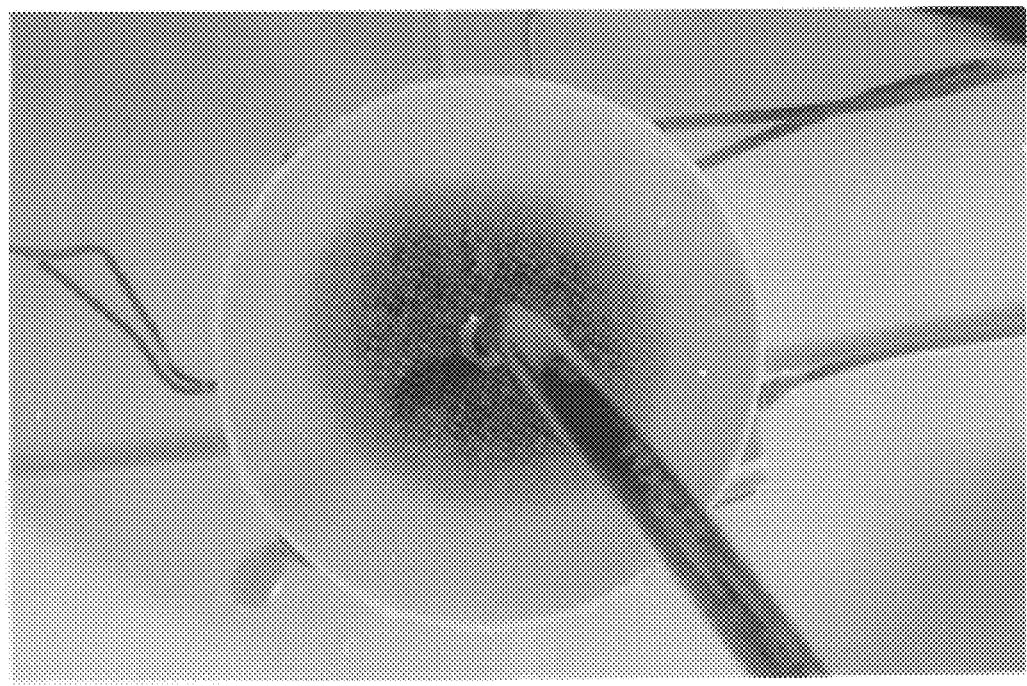
FIG. 27 is another photograph of dye injection into an uncreped, through-air-dried web of this invention.

FIGS. 26 and 27 have already been discussed above in connection with the In-Plane Permeability procedure.

EXAMPLES

Examples 1–4

In order to illustrate a method of making absorbent structures of this invention, paper sheets were produced using non-wet resilient northern softwood kraft fibers (NSWK), with and without a wet strength agent (20 lbs/ton Kymene), and wet resilient fibers (spruce BCTMP), with and without a wet strength agent (20 lbs/ton Kymene), using an uncreped throughdried process as described in FIG. 1.

The fiber was pulped at 4% consistency in the hydropulper for 30 minutes. The fiber was pumped into a stock chest and diluted to 1.0% consistency. 20#/ton of Kymene 557 LX was added to the stock chest and allowed to mix for 30 minutes. A single-layer, blended sheet of 30 gsm dry weight was formed on an Albany 94M forming fabric and dewatered with 5 inches (127 millimeters) of mercury vacuum. The forming fabric was traveling at 69 fpm (0.35 meters per second). The sheet was transferred at a 15% rush transfer to a Lindsay 952-S05 transfer fabric traveling at 60 fpm (0.30 meters per second). The vacuum in the transfer between the forming fabric and transfer fabric was 10 inches (254 millimeters) of mercury.

The sheet was vacuum transferred at 12 inches (305 millimeters) of mercury to a throughdryer fabric (Lindsay T116-1) traveling at the same speed as the transfer fabric, 60 fpm (0.30 meters per second). The sheet and throughdryer fabric traveled over a fourth vacuum at 12 inches (305 millimeters) of mercury just prior to entering a Honeycomb throughdryer operating at 200° F. (93° C.) and dried to a final dryness of 94–98% consistency.

The sheets were aged for over 5 days at less than 50% humidity at 70° F. (21° C.). The sheets were tested for physical characteristics in a controlled environment of 50%+2% humidity and 23° C.+10. The wet and dry strength were Instron tested with a 3-inch (7.62 cm) sample width, 4-inch (10.16 cm) jaw span at 10 in/min (25.4 cm/min) crosshead speed. Caliper was measured with the TMI tester at 0.289 psi.

Examples 5–8

Further examples were carried out similar to those described in Examples 1–4, but for the purpose of exploring the basis weight effect on a bulky, absorbent, wet resilient structure. Four basis weight levels of 30, 24, 18 and 13 gsm of 100% Spruce BCTMP with 20#/ton Kymene were produced.

The fiber was pulped at 4% consistency in the hydropulper for 30 minutes. The fiber was pumped into a stock chest and diluted to 1.0% consistency. 20#/ton of Kymene 557 LX was added to the stock chest and allowed to mix for 30 minutes. A single-layer, blended sheet was formed on an Albany 94M forming fabric and dewatered with 4 inches (102 millimeters) of mercury vacuum. The forming fabric was traveling at 69 fpm (0.35 meters per second). The sheet was transferred at a 15% rush transfer to a Lindsay 952-S05 transfer fabric traveling at 60 fpm (0.30 meters per second). The vacuum in the transfer between the forming fabric and transfer fabric was 7 inches (178 millimeters) of mercury. The 13 gsm sample was produced without a rush transfer, the forming fabric was traveling at 60 fpm (0.30 meters per second), the same as the transfer fabric and throughdryer fabric.

The sheet was vacuum transferred at 10 inches (254 millimeters) of mercury to a throughdryer fabric (Lindsay T116-1) traveling at the same speed as the transfer fabric, 60 fpm (0.30 meters per second). The sheet and throughdryer fabric traveled over a fourth vacuum at 11 inches (279 millimeters) of mercury just prior to entering a Honeycomb throughdryer operating at 260° F. (127° C.) and dried to a final dryness of 94–98% consistency.

The sheets were aged for over 5 days at less than 50% humidity at 70° F. (21° C.). The sheets were tested for physical characteristics in a controlled environment of 50%+

|  | Example 1 | Example 2 | Example 3 | Example 4 |
|---|---|---|---|---|
| Furnish | NSWK | NSWK | Spruce BCTMP | Spruce BCTMP |
| Kymene | 0 | 20#/ton | 0 | 20#/ton |
| MD grams dry | 1592 | 2761 | 1678 | 2257 |
| MD % stretch dry | 7.6 | 10.0 | 1.8 | 1.8 |
| CD grams dry | 1671 | 2459 | 1540 | 1872 |
| CD % stretch dry | 5.0 | 5.7 | 3.5 | 3.2 |
| GMT grams dry | 1631 | 2606 | 1608 | 2056 |
| MD grams wet | 106 | 892 | 49 | 826 |
| MD % stretch wet | 13.4 | 8.8 | 6.8 | 3.2 |
| CD grams wet | 71 | 715 | 47 | 759 |
| CD % stretch wet | 9.0 | 5.3 | 5.5 | 3.2 |
| GMT grams wet | 87 | 798 | 48 | 792 |
| MD % wet/dry | 6.6 | 32.3 | 2.9 | 36.6 |
| CD % wet/dry | 4.2 | 29.1 | 3.1 | 40.5 |
| GMT % wet/dry | 5.3 | 30.6 | 3.0 | 38.5 |
| Basis weight gsm | 31.7 | 32.2 | 32.4 | 32.7 |
| 1-Sheet TMI mm | .602 | .605 | .630 | .602 |
| 10-Sheet TMI mm | 3.34 | 3.68 | 3.91 | 3.95 |
| Density, g/cc | .053 | .053 | .051 | .054 |
| Bulk cc/g | 19.0 | 18.8 | 19.4 | 18.4 |
| Absorbency @ 0.075 psi | 7.6 | 8.7 | 10.2 | 10.1 |
| Horizontal g/g | 7.1 | 7.6 | 9.7 | 9.3 |
| 45° g/g |  |  |  |  |
| Percent Wet Wrinkle Recovery | 34.4 | 52.7 | 35.0 | 81.6 |

As shown, Example 4 (this invention) exhibited substantially greater wet resiliency, as measured by the Wet Wrinkle Recovery Test, than the other three samples. In addition, Example 4 also showed a high wet:dry ratio.

2% humidity and 23° C.+1°. The wet and dry strength were Instron tested with a 3-inch (7.62 cm) sample width, 4 inch (10.16 cm) jaw span at 10 in/min (25.4 cm/min) crosshead speed. The caliper was measured with the TMI tester at 0.289 psi. (The only difference in this example from the previous example is the vacuum level and dryer temperature).

|  | Example 5 | Example 6 | Example 7 | Example 8 |
|---|---|---|---|---|
| Basis Weight | 13 gsm | 18 gsm | 24 gsm | 30 gsm |
| MD grams dry | 1167 | 649 | 1091 | 1605 |
| MD % stretch dry | 1.4 | 3.7 | 4.0 | 5.1 |
| CD grams dry | 630 | 727 | 1130 | 1624 |
| CD % stretch dry | 2.6 | 3.5 | 4.0 | 4.0 |
| GMT grams dry | 857 | 687 | 1110 | 1614 |
| MD grams wet | 393 | 294 | 465 | 671 |
| MD % stretch wet | 1.5 | 5.0 | 5.5 | 5.5 |
| CD grams wet | 223 | 251 | 429 | 586 |
| CD % stretch wet | 2.4 | 3.3 | 3.5 | 3.5 |
| GMT grams wet | 296 | 272 | 447 | 627 |
| MD % wet/dry | 33.7 | 45.3 | 42.6 | 41.8 |
| CD % wet/dry | 35.4 | 34.5 | 38.0 | 36.1 |
| G#T % wet/dry | 34.5 | 40.0 | 40.3 | 38.8 |
| Basis weight gsm | 13.6 | 17.6 | 23.9 | 30.1 |
| 1-Sheet TMI, mm | .335 | .533 | .610 | .655 |
| 10-Sheet TMI, mm | 1.94 | 2.91 | 4.00 | 4.55 |
| Bulk cc/g | 24.6 | 30.3 | 25.5 | 21.8 |
| Absorbency @ 0.075 psi |  |  |  |  |
| Horizontal g/g | 12.2 | 13.3 | 13.0 | 11.8 |
| 45° g/g | 11.4 | 11.8 | 11.3 | 10.2 |
| Density, g/cc | .041 | .033 | .039 | .046 |
| Percent Wet Wrinkle Recovery | 73.8 | 76.7 | 85.0 | 86.7 |

As shown, all examples exhibited high wet resiliency as determinated by the Wet Wrinkle Recovery Test.

Examples 9–12

In order to further illustrate this invention, uncreped throughdried tissues were produced using the method substantially as illustrated in FIG. 1. More specifically, single-layer, single-ply tissues were made in which all layers comprised unrefined northern softwood bleached chemithermomechanical pulp (BCTMP) fibers. Prior to formation, the BCTMP fibers were pulped for 20 minutes at 4.6 percent consistency and diluted to 2.8 percent consistency after pulping. Kymene 557LX was added at 10–18 kilograms per metric ton of pulp.

A four-layer headbox was used to form the wet web with the unrefined northern softwood BCTMP stock in all four layers. Turbulence-generating inserts recessed about 3 inches (75 millimeters) from the slice and layer dividers extending about 6 inches (150 millimeters) beyond the slice were employed. Flexible lip extensions about 6 inches (150 millimeters) beyond the slice were also used, as taught in U.S. Pat. No. 5,129,988 issued Jul. 14, 1992 to Farrington, Jr. and entitled "Extended Flexible Headbox Slice With Parallel Flexible Lip Extensions And Extended Internal Dividers", which is hereby incorporated by reference. The net slice opening was about 0.75 inch (19 millimeters), and water flows in all four headbox layers were comparable. The consistency of the stock fed to the headbox was ranged from about 0.3 to about 0.5 weight percent.

The resulting single-layered sheet was formed on a twin-wire, suction form roll former in which both forming fabrics (12 and 13 in FIG. 1) were Asten 866 fabrics. The speed of the forming fabrics ranged from 5.3 to 6.6 meters per second. The newly-formed web was then dewatered to a consistency of about 20–27 percent using vacuum suction from below the forming fabric before being transferred to the transfer fabric, which was traveling from 3.6 to 5.1 meters per second. The resulting rush transfer ranged between 30 percent and 50 percent. The transfer fabric was a Lindsay 2164 fabric. A vacuum shoe pulling about 6–15 inches (150–380 millimeters) of mercury vacuum was used to transfer the web to the transfer fabric.

The web was then transferred to a throughdrying fabric (Lindsay Wire T116-3). The throughdrying fabric was traveling at a speed substantially the same as the transfer fabric. The web was carried over a Honeycomb throughdryer operating at a temperature of about 400° F. (204° C.) and dried to final dryness of about 94–98 percent consistency. The resulting uncreped throughdried tissue sheets had the following properties:

|  | Example 9 | Example 10 | Example 11 | Example 12 |
|---|---|---|---|---|
| Kymene, kg/MT | 10 | 18 | 10 | 10 |
| Rush Transfer, % | 30 | 30 | 30 | 50 |
| Forming Fabric Speed, M/S | 6.6 | 6.6 | 5.9 | 5.3 |
| Transfer Fabric Speed, M/S | 5.1 | 5.1 | 4.6 | 3.6 |
| Forming Consistency, % | 0.3 | 0.4 | 0.4 | 0.5 |
| MD grams dry | 4040 | 6340 | 7360 | 6190 |
| MD % stretch dry | 22.0 | 24.4 | 24.6 | 40.3 |
| CD grams dry | 2940 | 6560 | 4690 | 5140 |
| CD % stretch dry | 5.3 | 4.0 | 4.7 | 4.1 |

-continued

|  | Example 9 | Example 10 | Example 11 | Example 12 |
|---|---|---|---|---|
| GMT grams dry | 3446 | 6449 | 5875 | 5640 |
| MD grams wet | 2702 | 4383 | 3786 | 3562 |
| MD % stretch wet | 20.5 | 21.5 | 20.5 | 36.0 |
| CD grams wet | 1252 | 2840 | 1917 | 2101 |
| CD % stretch wet | 6.8 | 4.7 | 5.7 | 5.6 |
| GMT grams wet | 1839 | 3528 | 2694 | 2736 |
| MD % wet/dry | 66.9 | 69.1 | 51.4 | 57.5 |
| CD % wet/dry | 42.6 | 43.3 | 40.9 | 40.9 |
| GMT % wet/dry | 53.4 | 54.7 | 45.9 | 48.5 |
| Basis weight gsm | 65.2 | 82.8 | 88.8 | 109 |
| 1-Sheet TMI mm | 0.899 | 0.884 | 0.950 | 1.01 |
| 10-sheet TMI mm | 7.01 | 7.21 | 7.89 | 8.92 |
| Bulk cc/g | 13.8 | 10.7 | 10.7 | 9.27 |
| Absorbency @ .075 psi |  |  |  |  |
| Horizontal g/g | 10.8 | 8.3 | 8.3 | 7.6 |
| 450 g/g | 8.8 | 7.4 | 6.9 | 6.8 |
| Density g/cc | 0.073 | 0.094 | 0.093 | 0.108 |
| Percent wet Wrinkle Recovery | 75.0 | 83.9 | 78.9 | — |

As shown, all three examples for which the Wet Wrinkle Recovery Test was measured exhibited high wet resiliency as measured by that test.

In order to further illustrate the properties of the absorbent structures of this invention, the wet compressive resiliency properties of some of the foregoing samples were measured and are set forth below.

"HBAFF" is a softwood kraft fiber which has been chemically crosslinked with a urea-glyoxal resin. It is produced by Weyerhaeuser Comp. and is commercially available. HBAFF has a Water Retention Value of approximately 0.5 g/g.

"Curly-Q" fibers are taken from the transfer layer of 1993 Pampers diapers made by the Procter and Gamble Company.

| Wet Compressive Resiliency | | | | | | | | | | |
|---|---|---|---|---|---|---|---|---|---|---|
| | Example | | | | | | | | | |
| | 1 | 2 | 3 | 4 | 6 | 7 | 8 | 9 | 10 | 12 |
| Basis Weight, gsm | 31.7 | 32.2 | 32.4 | 32.7 | 17.6 | 23.9 | 30.1 | 65.2 | 82.8 | 109 |
| A) Initial Bulk @ 0.025 psi | 18.4 | 18.5 | 19.9 | 21.3 | 28.7 | 22.9 | 21.2 | 15.2 | 12.5 | 11.0 |
| B) Compressed Bulk | 5.2 | 6.0 | 7.1 | 7.9 | 8.2 | 8.1 | 8.0 | 8.7 | 8.0 | 7.7 |
| C) Final Bulk @ 0.025 psi | 8.4 | 13.6 | 13.0 | 18.0 | 22.7 | 19.3 | 17.7 | 14.1 | 11.4 | 10.2 |
| Compression Ratio (B/A) | 0.28 | 0.32 | 0.36 | 0.37 | 0.286 | 0.345 | 0.378 | 0.571 | 0.639 | 0.704 |
| Springback Ratio (C/A) | 0.46 | 0.73 | 0.66 | 0.85 | 0.791 | 0.841 | 0.838 | 0.929 | 0.917 | 0.926 |
| Loading Energy Ratio | 0.49 | 0.65 | 0.65 | 0.83 | 0.802 | 0.783 | 0.808 | 0.835 | 0.819 | 0.822 |

As shown, the examples of this invention (Examples 4–12) all exhibit high Springback Ratios and high Loading Energy Ratios compared to the controls (Examples 1–3). In addition, some of the examples of this invention also exhibited a high Wet Compressed Bulk of about 7.5 cc/g or greater (Examples 9, 10 and 12). Also, the examples of this invention presented above all exhibit Compression Ratios of about 0.7 or less in combination with Springback Ratios of about 0.8 or greater and Loading Energy Ratios of about 0.7 or greater, resulting in a web having a low wet modulus and high wet resiliency.

Examples U1–U10

To further illustrate the properties of the webs of this invention (Samples U1—U11) relative to other types of webs, comparative testing was carried out on uncreped through-air-dried webs made with different fibers, as well as comparing the properties of different types of webs. Some of the materials and the process conditions for Samples U1–U11 are summarized in the table of FIG. 10. The various fiber types and different types of webs tested are identified below:

Citric acid is used as a crosslinking agent. In addition to being chemically stiffened through crosslinking, the fibers are highly twisted and curled, giving additional bulk and resiliency to fluff pads made from the material. Curly-Q fibers have a Water Retention Value of approximately 0.4 g/g. The method of manufacture of these fibers is believed to be disclosed in part in the following U.S. patents: C. M. Herron, D. J. Cooper, T. R. Hanser, and B. S. Hersko, "Process for Preparing Individualized, Polycarboxylic Acid Crosslinked Fibers," U.S. Pat. No. 5,190,563 (1993 ); G. A. Young, D. R. Moore, J. T. Cook, "Absorbent Structures Containing Superabsorbent Material and Web of Wetlaid Stiffened Fibers," U.S. Pat. No. 5,217,445 (1993 ); J. T. Cook, G. R. Lash, D. R. Moore, ad G. A. Young, "Absorbent Structures Containing Stiffened Fibers and Superabsorbent Material," U.S. Pat. No. 5,360,420 (1994). "Curly-Q" fiber samples are labeled with prefixes of "CQ."

CR-1654 is a softwood pulp produced largely from southern pine at the Coosa River mill in Alabama. CR-1654 fibers have a WRV of about 1.1 g/g.

"HPZ" is a commercial mercerized pulp made by Buckeye with a WRV value of about 0.87.

"LL-19" is a northern pine kraft fiber made at the Terrace Bay mill in Canada. It has a WRV value of about 1.0 g/g.

"Air-laid softwood" is an airlaid fluff pad made of blended southern softwood kraft fibers from the Kimberly-Clark Coosa River mill. Air laying was done in a pulsed-air device in which the fibers were dispersed by air flow alone and redeposited gradually into a 4-inch wide mat lying on top of a thin tissue sheet.

Several commercial products used for testing were purchased from stores in Wisconsin, including "Viva Ultra" (1996), "Quilted Bounty" (1996)(printed and unprinted varieties), and "Brawny" towels (1994). Viva Ultra is a paper towel produced by the Scott Paper Company and is made with latex binder for high wet strength. Brawny is a paper towel product from the James River Company. Printed Quilted Bounty and unprinted Quilted Bounty are paper towel products from the Procter and Gamble Company, made with a mixture of fiber types including a percentage of CTMP pulp and added wet strength resins. Quilted Bounty purchased in mid-1994 was also used in additional testing.

Another commercial product used in testing is the "SURPASS®" handtowel from Kimberly-Clark Corporation, which is made with an uncreped, through-air dried process and with added wet-strength agents according to the patent of R. F. Cook and D. S. Westbrook, "Non-creped Hand or Wiper Towel," U.S. Pat. No. 5,048,589, issued Sep. 17, 1991. The Surpass towel is a typical example of uncreped, through-air dried technology without the improvements of the present invention; namely, a highly three-dimensional drying fabric with the additional synergistic combination of wet resilient fibers and wet strength agents. Samples from both 1995 and 1994 were used.

Three other materials were manufactured with the uncreped through-air dried process of the present invention, but without the synergistic combination of high wet strength and wet resilient fibers (high yield fibers). One such material is a 40 gsm tissue sheet made of northern softwood kraft fibers (LL-19) on a Lindsay wire T116-3 through-drying fabric, with 20 pounds of added Kymene per ton of dry fiber. The sheet was manufactured on a pilot tissue machine. This material is hereafter labeled as Sample O2. Another material was made in the same way but with spruce BCTMP fibers and no added Kymene, at a basis weight of 60 gsm. This material is labeled as Sample O3. A third material is similar to sample O2, but made at a basis weight of 60 gsm with 10 lb/ton of Kymene, hereafter labeled sample O4.

Figure 12:
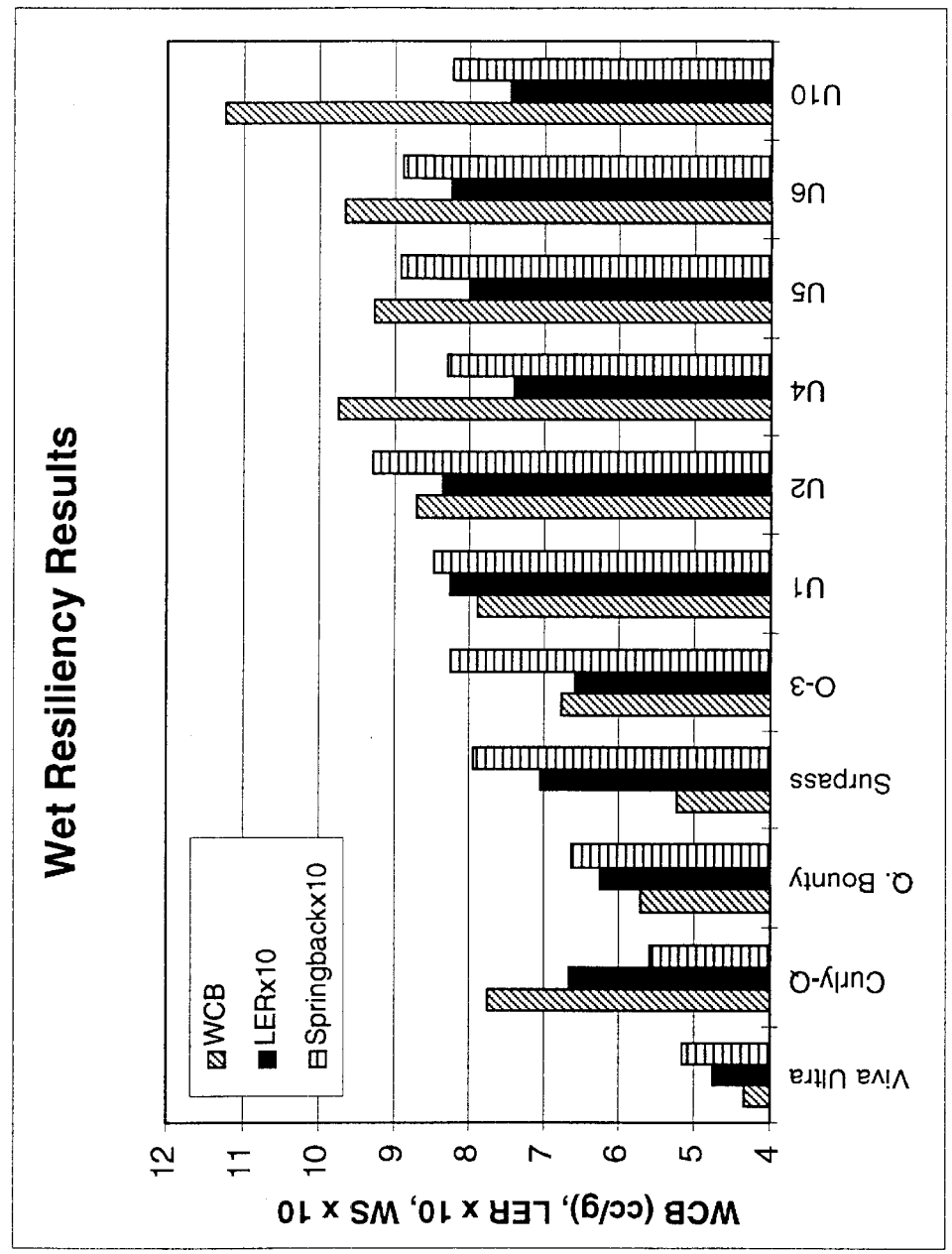
FIG. 12 is a bar chart summarizing the wet resiliency testing.
Figure 16:
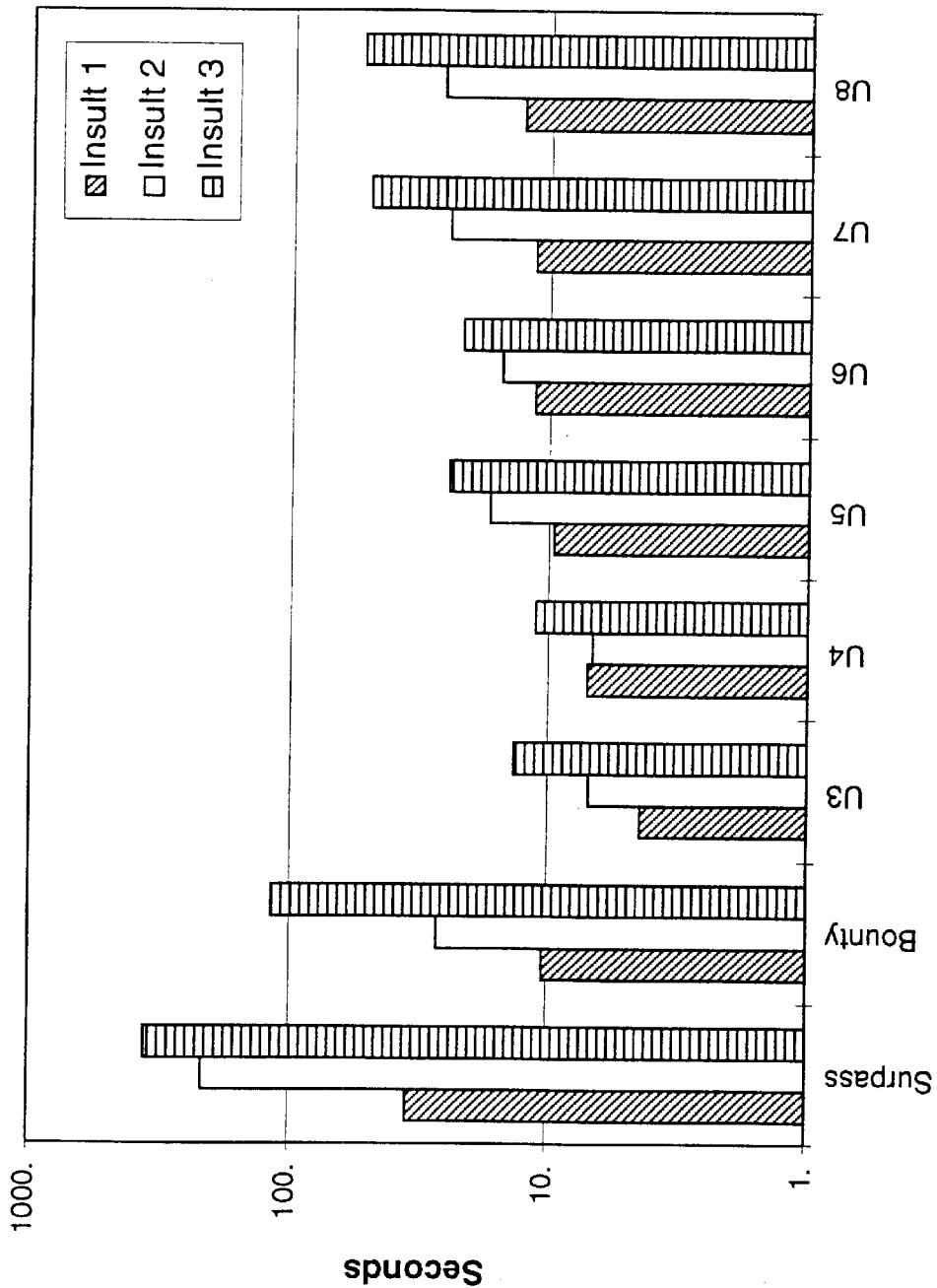
FIG. 16 is a bar chart illustrating the FIFE test results of FIG. 14.
Figure 17:
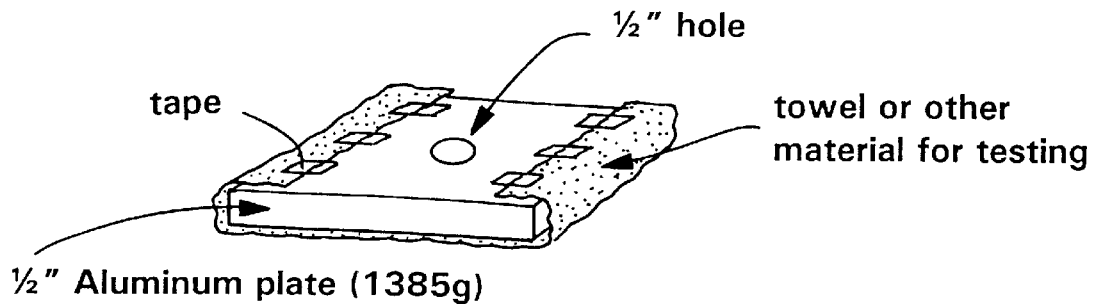
FIG. 17 is a perspective sketch of the sample prepared for testing in the Dry Wipe Residue test.
Figure 18:
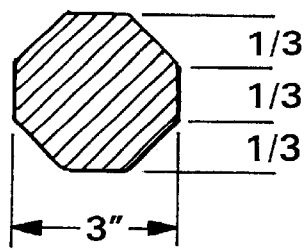
FIG. 18 is a plan view of the octagonal sample cut for the Wet Wipe Residue test.
Figure 19:
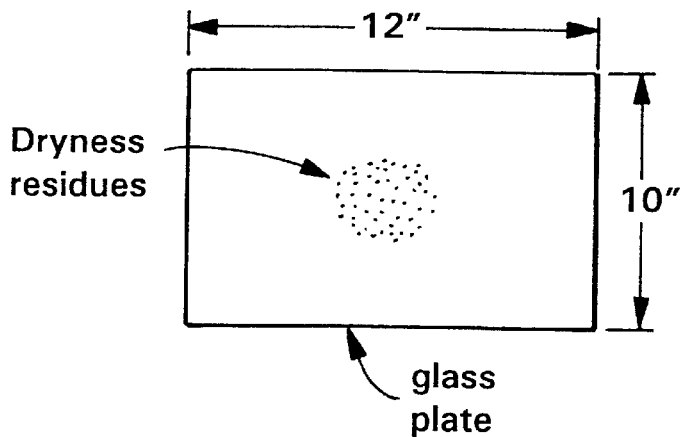
FIG. 19 is a schematic plan view of the glass plate showing the dryness residues to be measured for the Wet Wipe Residue test.

The wet resiliency of the materials of the present invention is compared to several other materials in the table of FIG. 11. Specifically, the table of FIG. 11 shows that the materials of the present invention can have exceptional Wet Compressed Bulk (WCB) values relative to other wet laid materials. Values of 7 cc/g and higher are achieved, while other wet laid products investigated have Wet Compressed Bulk values less than 7. Sample U10 has a WCB of about 11 cc/g. This sample also has a wet:dry strength ratio of about 0.5 and was produced at 50 percent rush transfer. Further, the materials of the present invention have high Wet Springback Ratio (WS) values, typically 0.8 or greater, with the value of Sample U2 exceeding 0.9 . Creped materials seem incapable of achieving such high wet resiliency. The LER values are also unusually high for the materials of the present invention, typically in excess of 0.7 and sometimes above 0.8. Some other materials may exhibit high values for one or two of the three wet resiliency parameters considered here, but the materials of the present invention are especially novel in displaying high values for all three parameters simultaneously. FIG. 12 is a bar chart that compares all three wet resiliency parameters for several other materials (including some air-laid materials to be discussed below) and for several materials of the present invention, showing again the unusual combination of high wet resiliency in all three parameters.

In addition to the materials listed in FIG. 11, several replicate runs with Quilted Bounty from 1994 were run, yielding a mean LER of 0.65, a mean Wet Springback ratio of 0.66, and a mean WCB of 6.14. A run with a stack of three 1994 Surpass handtowels yielded an LER of 0.66, a Wet Springback ratio of 0.75, and a WCB of 5.9. These values are similar to those for the related materials reported in Table 2.

To illustrate the wet resiliency of additional materials, details of wet resiliency measurements are discussed for several air laid materials incorporating chemically stiffened fibers. Important values from specific runs are shown in the table of FIG. 13. In gathering the data for this table, three types of fibers were used in these examples. Samples labeled with "CQ" were taken from 1993 Pampers® diapers made by the Procter and Gamble company. These chemically stiffened fibers are crosslinked with citric acid to yield a stiff fiber. In addition to being chemically stiffened through crosslinking, the fibers are highly twisted and curled, giving additional bulk and resiliency to fluff pads made from the material. HBAFF has a Water Retention Value of approximately 0.4 g/g.

In moistening airlaid pads, the surfaces of the pad were lightly blotted with facial tissue after spraying to remove any unabsorbed or excess moisture from the outer surfaces. Measurements have also been made in which the sample was allowed to sit for several hours to allow equilibration of moisture content, though longer equilibration times seemed to have no clear effect on the wet resiliency measurements.

After preliminary work revealed the low Wet Springback Ratio values obtained by typical airlaid cellulose, it was hypothesized that precompression could create a denser web that might have better Wet Springback Ratio values. Thus, some air-laid samples were precompressed and then tested. Minor gains in Wet Springback Ratios were possible with this strategy, at the expense of Wet Compressed Bulk. In the case of chemically stiffened fibers, moistening the precompressed sample results in an increase in bulk (especially when the fibers are curled and twisted, for they straighten out to a degree upon wetting and can then increase the bulk of a calendered or precompressed web, as taught by Cook et al. in U.S. Pat. No. 5,360,420, previously cited).

Some of the runs in Table 14 involved special procedures. Prior to testing, Sample CQ-A had been precompressed to a load of about 18 kg (40 pounds) by the Instron compression platens (giving 10 psi over the 2.25-inch diameter circular target area). After Sample CQ-A was dried and had reached room temperature, the entire dry sample was uniformly loaded under a 35 kg weight (giving a pressure of about 12 psi) for about 30 seconds. It was then tested again for wet resiliency, giving run CQ-A2. After drying and cooling, this sample was again tested for wet resiliency, resulting in run CQ-A3. Samples CQ-B and CQ-C were tested in the normal manner, without precompression, with the exception that Sample CQ-C experienced a delay of about 5 minutes from the beginning of moistening to the beginning of the wet compression test. Sample CQ-D was precompressed under a 15 kg weight (33 lb, for a pressure of about 5.3 psi) for about 30 seconds and was allowed to equilibrate in the moistened state while in a plastic bag for about 15 minutes before the wet compression test began. Sample CQ-E was precompressed by the Instron compressive platens to a pressure of 10–12 psi for about 90 seconds, followed by a pressure of 25 psi for about 10 seconds. The sample then sat uncompressed for 1 minute prior to testing. (Again, the compressive testing involves a first series of compressions in the dry state, followed by moistening and then a second identical series of compressions in the moist state.) Sample CQ-F was tested in the normal manner.

The results in the table of FIG. 13 again show that some other materials may achieve high values for WCB, but are unable to simultaneously provide WS and LER values comparable to the materials of the present invention. The combination of high z-direction fiber orientation from air forming plus the stiff and somewhat water-insensitive nature of these fibers yields relatively good wet bulk under compression (WCB values of 6 to 8.2). However, their intrinsic stiffness and brittleness not only makes them difficult to process but hinders their dynamic elastic properties when wet, resulting in poor LER and WS values (LER<0.75 and WS<0.7).

The table of FIG. 14 summarizes In-Plane Permeability results for materials made in accord with the present invention (having sample labels beginning with "U") as well as materials outside the scope of the present invention (sample labels beginning with "P"). For materials of the present invention are reported for the case of two plies, the table of FIG. 14 shows details of the process used, including the Kymene add on, the through-drying fabric type (fabrics from Lindsay wire), the percent of differential velocity (rush) transfer. For all materials in FIG. 14, the In-Plane Permeability and the bulk of the wet sheet at 0.8 psi are shown.

Materials outside the scope of the present invention include Surpass towel, which is an uncreped, through-air dried towel produced by Kimberly-Clark for industrial and commercial use. Quilted Bounty is a commercial, high-bulk, creped through-air-dried towel product from the Proctor and Gamble Company, which contains some BCTMP fiber and wet strength agents, but lacks the pore structure, wet resiliency, and three-dimensional structure of the present invention.

Several air-laid fluff pads were examined. Air-laying is often said to be especially advantageous for maintaining high bulk and an open, permeable structure because it results in many z-direction fibers which can resist compression and hold the sheet open, especially when stiffened fibers are used. Two sources of chemically stiffened fibers were used to produce air-laid sheets for testing. The first source is HBAFF fluff, a commercial cross-linked wood fiber pulp produced by Weyerhaeuser Company. The other is "CurlyQ" fibers taken from the transfer layer of 1993 Pampers diapers, produced by the Proctor and Gamble Company. Both of these fiber types are much stiffer and have higher wet bulk than is possible with untreated or conventional fluff pulps or air-laid sheets, but neither can provide the high In-Plane Permeability of the present invention. Samples P6 and P7 are two forms of conventional fluff pulp. Sample P6 is from a continuous operation for producing fluff pulp on a tissue backing sheet, while sample P7 is from an air-laying batch operation. Sample P5 is an uncreped, through-dried sheet of hardwood produced without wet strength resins.

The materials of the present invention show higher permeability than is possible with other wet laid processes and also show higher permeability than is achieved by air-laying of conventional or chemically stiffened fibers. The increased permeability is due in part to the excellent wet resiliency of the three-dimensional structures, which maintains high bulk under compression. But the high bulk (and thus high pore space) does not account for all of the enhanced permeability. This can be seen by comparing Samples U8 and U9, with wet bulks under 8 cc/g, to Samples P3 and P4, which have similar or higher wet bulks yet have significantly lower in-plane permeabilities. The higher in-plane permeability of the materials of the present invention is believed to be partially due to the nature of the pore size distribution, which provides a combination of microscopic pores and larger surface pores which provide less tortuous flow paths and lower resistance to in-plane flow. It is believed that this advantageous sheet and pore structure for in-plane flow is achieved by avoiding significant densification of the sheet during water removal and drying operations, by using rush transfer to create additional pore space distributed heterogeneously, and by using a three-dimensional throughdrying fabric to create texture.

The table of FIG. 15 summarizes the FIFE test data for some of the samples previously identified. These same results are presented in the bar chart of FIG. 16. As these results illustrate, for all three insults, the materials of the present invention allow rapid distribution of the fluid. The Surpass and Bounty materials require substantially more time.

The table of FIG. 20 summarizes the Dry Wipe Residue data comparing the webs of this invention (Samples 3–8) with the prior art Bounty and Surpass towels. As the results illustrate, the webs of this invention leave a residue that covers a lower percentage of the area tested than do the prior art samples. Also, the residue Mass Factor for the webs of this invention are also significantly lower. The low residue values suggest that these materials might be well suited for keeping fluid away from the user's skin in absorbent articles, and also point to the possible utility of such materials in articles for cleaning and wiping.

The table of FIG. 21 summarizes the Wet Wipe Residue data for the same samples of FIG. 20. As shown, the webs of this invention again leave behind a smaller residue area coverage and a lower Mass Factor than the prior art samples.

Figures 22, 23:
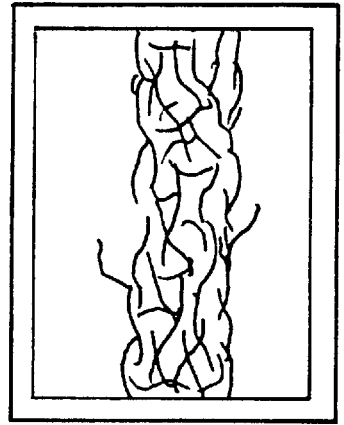
FIG. 22 is a table summarizing the results of the Mean Volume-Weighted Pore Length tests.
FIG. 23 is a representation of a typical cross-sectional photo used to analyze the Mean Volume-Weighted Pore Length.

The table of FIG. 22 summarizes some structural properties of the webs of this invention compared to the prior art. Specifically, the Mean Volume-Weighted Pore Length values for the webs of this invention are substantially larger than those of the prior art samples. Also, the Thickness Variation Index of the webs of this invention is substantially less than that of the Bounty sample, which is indicative of the differences between the uncreped throughdried method of making the webs of this invention and the more conventional creped, throughdried method used for making the Bounty product.

All of the foregoing examples serve to illustrate the unique wet-resiliency and absorbency properties of the novel cellulosic webs of this invention that make them especially well suited for use in absorbent articles and other products. However, it will be appreciated that the foregoing examples, given for purposes of illustration, are not to be considered as limiting the scope of this invention which is defined by the following claims and all equivalents thereto.

We claim:

1. A three-dimensional, throughdried uncreped cellulosic paper web comprising about 20 dry weight percent or more high yield pulp fibers and a wet strength agent, said paper web having a density of about 0.3 gram per cubic centimeter or less, a wet:dry ratio of about 0.10 or greater, an Overall Surface Depth of about 0.2 millimeter or greater, and a Wet Compressed Bulk of about 7 cubic centimeters or greater per gram.

2. An absorbent article comprising a backsheet layer, a liquid permeable topsheet layer connected in a superposed relation with said backsheet layer, and at least one through-air-dried uncreped tissue sheet sandwiched between said topsheet layer and backsheet layer, said through-air-dried sheet comprising at least about 20 dry weight percent high yield pulp fibers to which a wet strength agent has been added and having a density of about 0.3 grams per cubic centimeter or less, an Overall Surface Depth of about 0.3 millimeters or greater, and a Wet Compressed Bulk of about 7 cubic centimeters or greater per gram.

3. The absorbent article of claim 2 wherein the through-air-dried sheet has a Wet Compressed Bulk of about 7 cubic centimeters per gram or greater.

4. The absorbent article of claim 2 wherein the through-air-dried sheet has a FIFE Test value of about 125 seconds or less.

5. The absorbent article of claim 2 wherein the through-air-dried sheet has an In-Plane Permeability of about $4 \times 10^{-11}$ or greater.

6. The absorbent article of claim 2 further comprising an absorbent fluff batt of fibers adjacent the through-air-dried sheet.

7. The absorbent article of claim 2 having from 2 to about 20 through-air-dried sheets.

8. The absorbent article of claim 2 wherein the through-air-dried sheet is uncreped.

9. A three-dimensional, throughdried cellulosic uncreped paper web comprising about 20 dry weight percent or more high yield pulp fibers having a Water Retention Value of about 0.7 or greater and a wet strength agent, said paper web having a density of about 0.3 gram per cubic centimeter or less, a wet:dry ratio of about 0.10 or greater, an Overall Surface Depth of about 0.2 millimeter or greater, and a Wet Compressed Bulk of about 7 cubic centimeters or greater per gram.

10. The web of claim 9 wherein the Water Retention Value of the fibers is about 0.9 or greater.

11. The web of claim 9 wherein the Water Retention Value of the fibers is about 1 or greater.

12. The web of claim 9 wherein the Water Retention Value of the fibers is from about 0.9 to about 2.

13. An absorbent article comprising a backsheet layer, a liquid permeable topsheet layer connected in a superposed relation with said backsheet layer, and at least one uncreped through-air-dried tissue sheet sandwiched between said topsheet layer and backsheet layer, said through-air-dried sheet comprising at least about 20 dry weight percent high yield pulp fibers having a Water Retention Value of about 0.7 or greater to which a wet strength agent has been added and having a density of about 0.3 grams per cubic centimeter or less, an Overall Surface Depth of about 0.3 millimeters or greater, a wet:dry ratio of about 0.10 or greater and a Wet Compressed Bulk of about 7 cubic centimeters or greater per gram.

14. The absorbent article of claim 13 wherein the Water Retention Value of the fibers is about 0.9 or greater.

15. The absorbent article of claim 13 wherein the Water Retention Value of the fibers is about 1 or greater.

16. The absorbent article of claim 13 wherein the Water Retention Value of the fibers is from about 0.9 to about 2.

17. A three-dimensional, throughdried uncreped cellulosic paper web comprising about 20 dry weight percent or more high yield pulp fibers and a wet strength agent, said paper web having a density of about 0.3 gram per cubic centimeter or less, a wet:dry ratio of about 0.10 or greater, an Overall Surface Depth of about 0.2 millimeter or greater, and a Wet Compressed Bulk of about 7 cubic centimeters or greater per gram.

18. The web of claim 17 having a basis weight of from about 10 to about 80 grams per square meter.

19. The web of claim 17 having a basis weight of from about 20 to about 60 grams per square meter.

20. The web of claim 17 having a density of about 0.1 gram per cubic centimeter or less.

21. The web of claim 17 having a Wet Wrinkle Recovery of about 60 percent or greater.

22. The web of claim 17 having a Wet Wrinkle Recovery of about 70 percent or greater.

23. The web of claim 17 having a Wet Wrinkle Recovery of about 80 percent or greater.

24. The web of claim 17 having a wet:dry ratio of about 0.2 or greater.

25. The web of claim 17 having a wet:dry ratio of about 0.5 or greater.

26. The web of claim 17 having a Compression Ratio of from 0.4 to about 0.7.

27. The web of claim 17 having a Wet Springback Ratio of about 0.75 or greater.

28. The web of claim 17 having a Wet Springback Ratio of about 0.9 or greater.

29. The web of claim 17 having a Wet Springback Ratio of from about 0.8 to about 0.93.

30. The web of claim 17 having a Loading Energy Ratio of about 0.7 or greater.

31. The web of claim 17 having a Loading Energy Ratio of about 0.8 or greater.

32. The web of claim 17 having a Loading Energy Ratio of from about 0.7 to about 0.9.

33. The web of claim 17 having a Wet Compressed Bulk of about 7 cubic centimeters per gram or greater.

34. The web of claim 17 having a Wet Compressed Bulk of about 8 cubic centimeters per gram or greater.

35. The web of claim 17 having a Wet Compressed Bulk of from about 8 to about 13 cubic centimeters.

36. The web of claim 17 having a Wet Compressed Bulk of about 8 cubic centimeters per gram or greater, a Wet Springback ratio of about 0.8 or greater and a Loading Energy Ratio of about 0.7 or greater.

37. The web of claim 17 wherein the fibers of the web have a water retention value of about 0.9 or greater.

38. The web of claim 17 having an In-Plane Permeability of about $5 \times 10^{-11}$ square meters or greater.

39. The web of claim 17 having an In-Plane Permeability of from about $5 \times 10^{-11}$ to about $80 \times 10^{-11}$ square meters.

40. The web of claim 17 having an In-Plane Permeability of from about $8 \times 10^{-11}$ to about $30 \times 10^{-11}$ square meters.

41. The web of claim 17 having a FIFE Test value of about 125 seconds or less.

42. The web of claim 17 having a FIFE Test value of about 75 seconds or less.

43. The web of claim 17 having a Dry Wipe Residue Total Area coverage of about 2000 square millimeters or less.

44. The web of claim 17 having a Dry Wipe Residue Mass Factor of about 30 or less.

45. The web of claim 17 having a Wet Wipe Residue Total Area coverage of about 1500 square millimeters or less.

46. The web of claim 17 having a Wet Wipe Residue Mass Factor of about 5 or less.

47. The web of claim 17 having a Mean Volume-Weighted Pore Length of about 550 microns or greater.

48. The web of claim 17 having a Thickness Variation Index of about 25 percent or less.

49. The web of claim 17 having an Overall Surface Depth of from about 0.4 to about 0.8 millimeters.

50. An absorbent article comprising the web of claim 17.

51. A disposable diaper comprising the web of claim 17.

52. A feminine pad comprising the web of claim 17.

53. A meat and poultry pad comprising the web of claim 17.

54. A bed pad comprising the web of claim 17.

55. An absorbent article comprising a backsheet layer, a liquid permeable topsheet layer connected in a superposed relation with said backsheet layer, and at least one through-air-dried uncreped tissue sheet sandwiched between said topsheet layer and backsheet layer, said through-air-dried sheet comprising at least about 20 dry weight percent high yield pulp fibers to which a wet strength agent has been added and having a density of about 0.3 grams per cubic centimeter or less, an Overall Surface Depth of about 0.3 millimeters or greater, and a Wet Compressed Bulk of about 0.7 cubic centimeters or greater per gram.

56. The absorbent article of claim 55 wherein the through-air-dried sheet has a Wet Compressed Bulk of about 7 cubic centimeters per gram or greater.

57. The absorbent article of claim 55 wherein the thorough-air-dried sheet has a FIFE Test value of about 125 seconds or less.

58. The absorbent article of claim 55 wherein the through-air-dried sheet has an In-Plane Permeability of about $4 \times 10^{-11}$ or greater.

59. The absorbent article of claim 55 further comprising an absorbent fluff batt of fibers adjacent the through-air-dried sheet.

60. The absorbent article of claim 55 having from about 2 to about 20 through-air-dried sheets.

61. The absorbent article of claim 55 wherein the through-air-dried sheet is uncreped.

62. A three-dimensional, throughdried cellulosic uncreped paper web comprising about 20 dry weight percent or more high yield pulp fibers having a Water Retention Value of about 0.7 or greater and a wet strength agent, said paper web having a density of about 0.3 gram per cubic centimeter or less, a wet:dry ratio of about 0.10 or greater, an Overall Surface Depth of about 0.2 millimeter or greater, and a Wet Compressed Bulk of about 0.7 cubic centimeters or greater per gram.

63. The web of claim 62 wherein the Water Retention Value of the fibers is about 0.9 or greater.

64. The web of claim 62 wherein the Water Retention Value of the fibers is about 1 or greater.

65. The web of claim 62 wherein the Water Retention Value of the fibers is from about 0.9 to about 2.

66. An absorbent article comprising a backsheet layer, a liquid permeable topsheet layer connected in a superposed relation with said backsheet layer, and at least one uncreped through-air-dried tissue sheet sandwiched between said topsheet layer and backsheet layer, said through-air-dried sheet comprising at least about 20 dry weight percent high yield pulp fibers having a Water Retention Value of about 0.7 or greater to which a wet strength agent has been added and having a density of about 0.3 grams per cubic centimeter or less, an Overall Surface Depth of about 0.3 millimeters or greater, a wet:dry ratio of about 0.10 or greater and a Wet Compressed Bulk of about 7 cubic centimeters or greater per gram.

67. The absorbent article of claim 66 wherein the Water Retention Value of the fibers is about 0.9 or greater.

68. The absorbent article of claim 66 wherein the Water Retention Value of the fibers is about 1 or greater.

69. The absorbent article of claim 66 wherein the Water Retention Value of the fibers is from about 0.9 to about 2.

\* \* \* \* \*

UNITED STATES PATENT AND TRADEMARK OFFICE
CERTIFICATE OF CORRECTION

PATENT NO.   : 6,436,234 B1                                              Page 1 of 1
DATED        : August 20, 2002
INVENTOR(S)  : Fung-jou Chen, Mark Alan Burazin, Michael Alan Hermans, David Henry Hollenberg,
               Richard Joseph Kamps, Bernhardt Edward Kressner and Jeffrey Dean Lindsay It is certified that error appears in the above-identified patent and that said Letters Patent is
hereby corrected as shown below:

Column 23,
Line 32, insert -- * -- after the first occurrence of "CAL. CONST".

Column 44,
Line 63, delete "uncreped".
Line 64, delete "paper".

Column 45,
Line 7, delete "uncreped tissue".
Lines 31 and 32, delete "uncrepred paper".
Line 34, delete "paper".
Line 48, delete "uncreped".
Line 49, delete "tissue".
Line 56, delete ", a wet:dry ratio of about 0.10 or greater".

Signed and Sealed this

Twenty-fourth Day of December, 2002

JAMES E. ROGAN
*Director of the United States Patent and Trademark Office*